(12) United States Patent
Leeflang et al.

(10) Patent No.: US 8,252,015 B2
(45) Date of Patent: *Aug. 28, 2012

(54) EXPANDABLE GUIDE SHEATH AND APPARATUS AND METHODS FOR MAKING THEM

(75) Inventors: Stephen A. Leeflang, Sunnyvale, CA (US); Christine P. Ventura, San Jose, CA (US); Christian S. Eversull, Palo Alto, CA (US); Nicholas J. Mourlas, Mountain View, CA (US); Christopher Loew, Palo Alto, CA (US)

(73) Assignee: Medtronic, Inc., Minneapolis, MN (US)

( * ) Notice: Subject to any disclaimer, the term of this patent is extended or adjusted under 35 U.S.C. 154(b) by 220 days.

This patent is subject to a terminal disclaimer.

(21) Appl. No.: 12/715,517

(22) Filed: Mar. 2, 2010

(65) Prior Publication Data
US 2010/0160952 A1     Jun. 24, 2010

Related U.S. Application Data

(63) Continuation of application No. 10/958,034, filed on Oct. 4, 2004, now Pat. No. 7,713,281.

(60) Provisional application No. 60/551,901, filed on Mar. 9, 2004, provisional application No. 60/508,489, filed on Oct. 3, 2003, provisional application No. 60/508,490, filed on Oct. 3, 2003, provisional application No. 60/508,491, filed on Oct. 3, 2003.

(51) Int. Cl.
*A61M 29/00* (2006.01)

(52) U.S. Cl. ..... 606/194; 623/1.11; 623/1.12; 623/1.23; 600/184

(58) Field of Classification Search ............. 606/191, 606/194, 198, 192, 108, 193, 195, 196, 197, 606/199, 200; 623/1.11; 604/103.01, 509, 604/525, 528, 915; 600/184
See application file for complete search history.

(56) References Cited

U.S. PATENT DOCUMENTS

| | | | |
|---|---|---|---|
| 4,392,853 A | 7/1983 | Muto | |
| 4,401,433 A | 8/1983 | Luther | |
| 4,406,656 A | 9/1983 | Hattler et al. | |
| 4,451,256 A | 5/1984 | Weikl et al. | |
| 4,569,347 A | 2/1986 | Frisbie | |
| 4,581,017 A | 4/1986 | Sahota | |
| 4,601,713 A | 7/1986 | Fuqua | |
| 4,710,181 A | 12/1987 | Fuqua | |

(Continued)

FOREIGN PATENT DOCUMENTS

EP       818214 A1    1/1998

(Continued)

*Primary Examiner* — Gary Jackson
*Assistant Examiner* — Katrina Stransky

(57) ABSTRACT

An apparatus for providing access to a body lumen includes a tubular proximal portion and an expandable distal portion, which extends distally from a distal end of the proximal portion. The expandable distal portion includes an expandable sheath and a stiffening member. The proximal portion has a first lumen extending from a proximal end to a distal end thereof, and the expandable sheath defines a second lumen that is in fluid communication with the first lumen and extends distally from the proximal portion to a distal terminal opening of the second lumen. The stiffening member is attached directly to the expandable sheath so as to extend alongside the second lumen, and the distal terminal opening of the second lumen is defined by a portion of a perimeter of a distal terminal end of the expandable sheath that becomes spaced apart from the stiffening member when the sheath is expanded.

9 Claims, 29 Drawing Sheets

U.S. PATENT DOCUMENTS

| | | | |
|---|---|---|---|
| 4,738,666 A | 4/1988 | Fuqua | |
| 4,921,479 A | 5/1990 | Grayzel | |
| 4,995,878 A | 2/1991 | Rai | |
| 5,015,239 A | 5/1991 | Browne | |
| 5,137,519 A | 8/1992 | Littrell et al. | |
| 5,160,559 A | 11/1992 | Scovil et al. | |
| 5,176,660 A | 1/1993 | Truckai | |
| 5,201,756 A | 4/1993 | Horzewski et al. | |
| 5,209,728 A | 5/1993 | Kraus et al. | |
| 5,234,425 A | 8/1993 | Fogarty et al. | |
| 5,254,084 A | 10/1993 | Geary et al. | |
| 5,256,150 A | 10/1993 | Quiachon et al. | |
| 5,263,932 A | 11/1993 | Jang | |
| 5,267,958 A | 12/1993 | Buchbinder | |
| 5,275,151 A | 1/1994 | Shockey et al. | |
| 5,304,134 A | 4/1994 | Kraus | |
| 5,395,349 A | 3/1995 | Quiachon et al. | |
| 5,413,560 A | 5/1995 | Solar | |
| 5,431,676 A | 7/1995 | Dubrul et al. | |
| 5,472,418 A | 12/1995 | Palestrant | |
| 5,505,686 A | 4/1996 | Willis et al. | |
| 5,573,517 A | 11/1996 | Bonutti et al. | |
| 5,599,305 A | 2/1997 | Hermann et al. | |
| 5,618,267 A | 4/1997 | Palestrant | |
| 5,669,924 A | 9/1997 | Shaknovich | |
| 5,674,240 A | 10/1997 | Bonutti et al. | |
| 5,749,889 A | 5/1998 | Bacich | |
| 5,749,890 A | 5/1998 | Shaknovich | |
| 5,752,934 A | 5/1998 | Campbell | |
| 5,762,604 A | 6/1998 | Kieturakis | |
| 5,772,628 A | 6/1998 | Bacich | |
| 5,795,331 A | 8/1998 | Cragg et al. | |
| 5,810,776 A | 9/1998 | Bacich | |
| 5,824,041 A | 10/1998 | Lenker et al. | |
| 5,827,227 A | 10/1998 | DeLago | |
| 5,863,366 A | 1/1999 | Snow | |
| 5,908,435 A | 6/1999 | Samuels | |
| 5,910,154 A | 6/1999 | Tsugita et al. | |
| 5,911,702 A | 6/1999 | Romley et al. | |
| 5,935,122 A | 8/1999 | Fourkas et al. | |
| 5,944,691 A | 8/1999 | Querns et al. | |
| 5,961,499 A | 10/1999 | Bonutti et al. | |
| 5,972,441 A | 10/1999 | Campbell | |
| 5,997,508 A | 12/1999 | Lunn et al. | |
| 6,007,517 A | 12/1999 | Anderson | |
| 6,007,522 A | 12/1999 | Agro et al. | |
| 6,030,362 A * | 2/2000 | Boussignac et al. | 604/101.01 |
| 6,068,610 A | 5/2000 | Ellis et al. | |
| 6,090,072 A | 7/2000 | Kratoska | |
| 6,120,477 A | 9/2000 | Campbell et al. | |
| 6,179,827 B1 | 1/2001 | Davis | |
| 6,183,443 B1 | 2/2001 | Kratoska et al. | |
| 6,197,016 B1 | 3/2001 | Fourkas et al. | |
| 6,296,616 B1 | 10/2001 | McMahon | |
| 6,312,406 B1 | 11/2001 | Jayaraman | |
| 6,338,730 B1 | 1/2002 | Bonutti et al. | |
| 6,361,528 B1 | 3/2002 | Wilson et al. | |
| 6,743,196 B2 | 6/2004 | Barbut et al. | |
| 6,814,715 B2 | 11/2004 | Bonutti et al. | |
| 6,908,474 B2 | 6/2005 | Hogendijk et al. | |
| 7,399,307 B2 | 7/2008 | Evans et al. | |
| 7,575,569 B2 * | 8/2009 | Eversull et al. | 604/103.01 |
| 7,713,281 B2 * | 5/2010 | Leeflang et al. | 606/194 |
| 7,744,564 B2 * | 6/2010 | Eversull et al. | 604/103.01 |
| 7,762,995 B2 * | 7/2010 | Eversull et al. | 604/264 |
| 7,875,049 B2 * | 1/2011 | Eversull et al. | 606/198 |
| 7,993,350 B2 * | 8/2011 | Ventura et al. | 606/108 |
| 2001/0007927 A1 | 7/2001 | Koblish et al. | |
| 2001/0041909 A1 | 11/2001 | Tsugita | |
| 2001/0053919 A1 | 12/2001 | Kieturakis et al. | |
| 2002/0095117 A1 | 7/2002 | Wilson et al. | |
| 2002/0099431 A1 | 7/2002 | Armstrong et al. | |
| 2002/0123765 A1 | 9/2002 | Sepetka et al. | |
| 2002/0165598 A1* | 11/2002 | Wahr et al. | 623/1.11 |
| 2003/0004540 A1 | 1/2003 | Linder et al. | |
| 2003/0065353 A1 | 4/2003 | Horzewski et al. | |
| 2003/0233115 A1 | 12/2003 | Eversull et al. | |
| 2004/0006344 A1 | 1/2004 | Nguyen et al. | |
| 2004/0073286 A1 | 4/2004 | Armstrong et al. | |
| 2004/0087968 A1 | 5/2004 | Core | |
| 2004/0097788 A1 | 5/2004 | Mourlas et al. | |
| 2004/0167439 A1 | 8/2004 | Sharrow | |
| 2005/0008584 A1 | 1/2005 | Montgomery | |

FOREIGN PATENT DOCUMENTS

| | | |
|---|---|---|
| WO | 8401512 A1 | 4/1984 |
| WO | 9729680 A1 | 8/1997 |
| WO | 9829026 A1 | 7/1998 |
| WO | 03090834 A1 | 11/2003 |

* cited by examiner

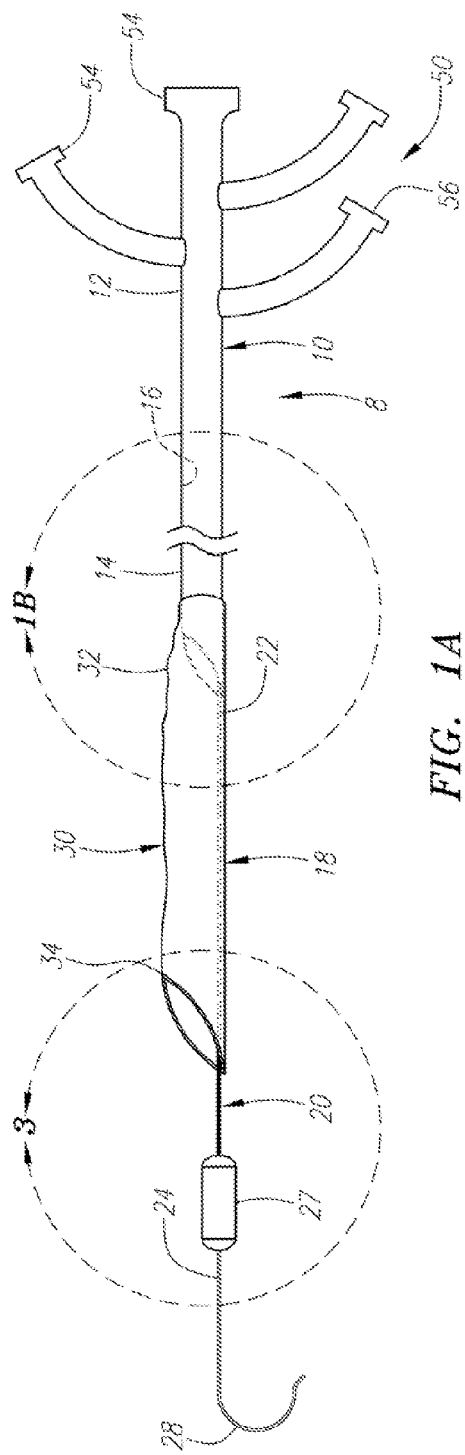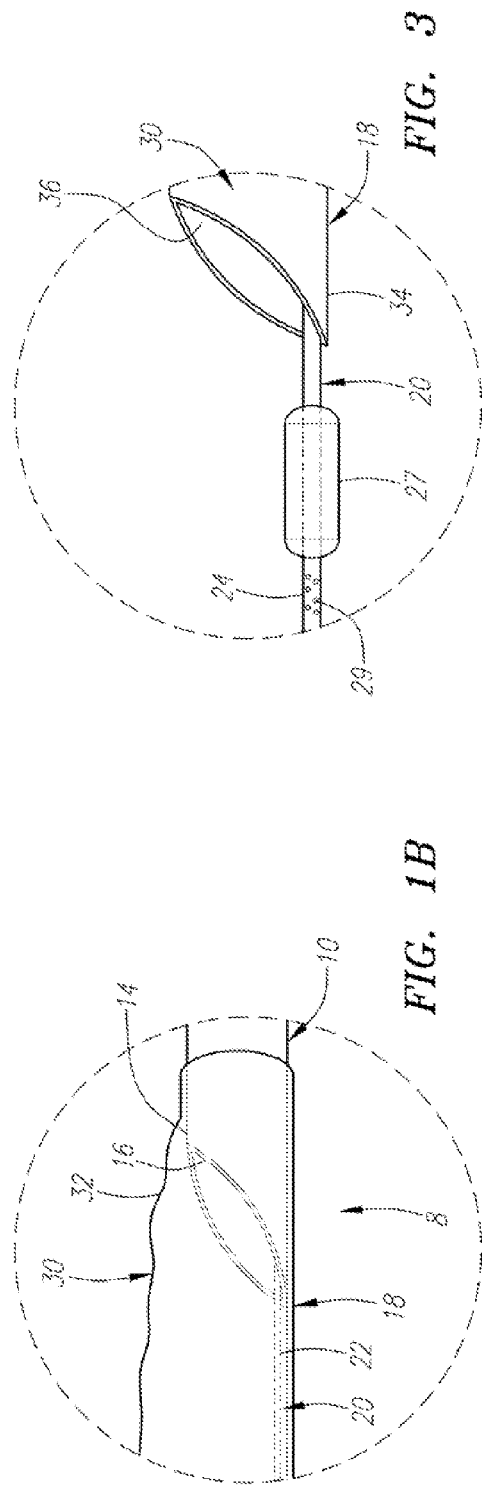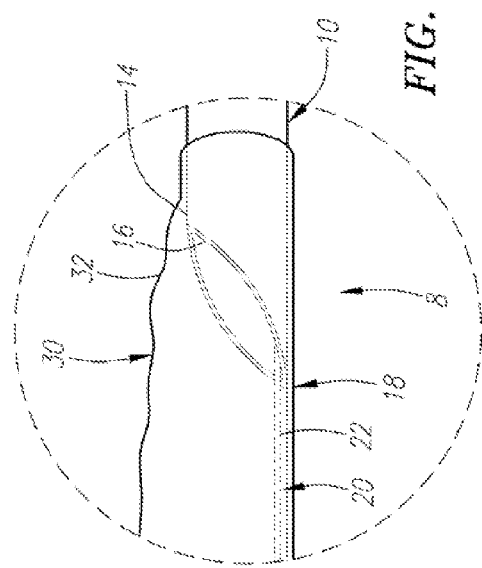

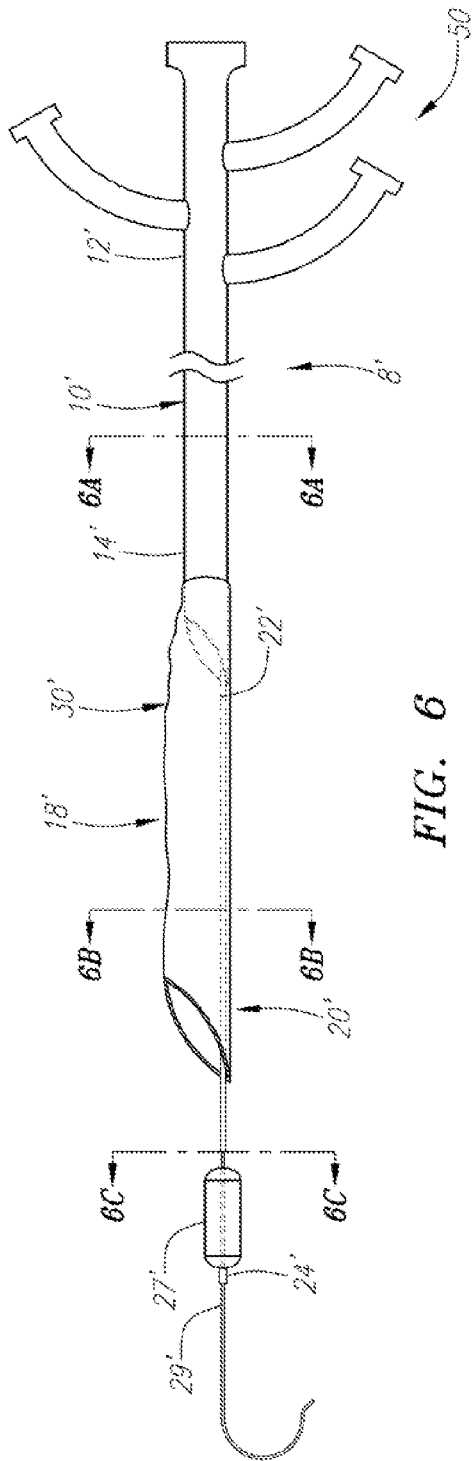
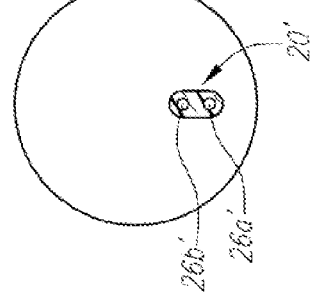
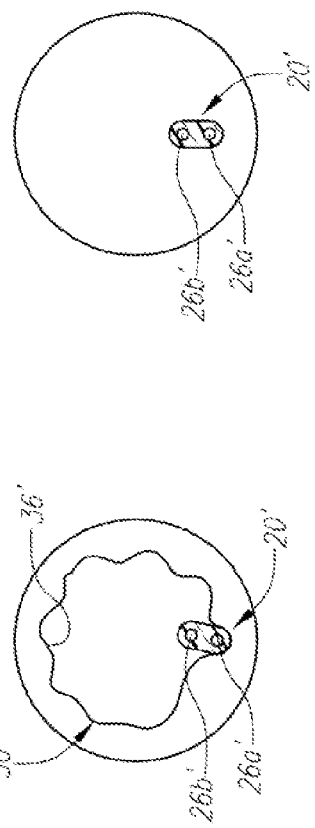
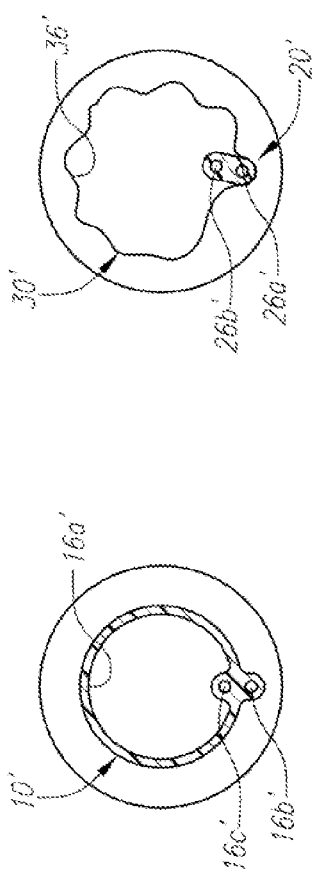
FIG. 6
FIG. 6A
FIG. 6B
FIG. 6C

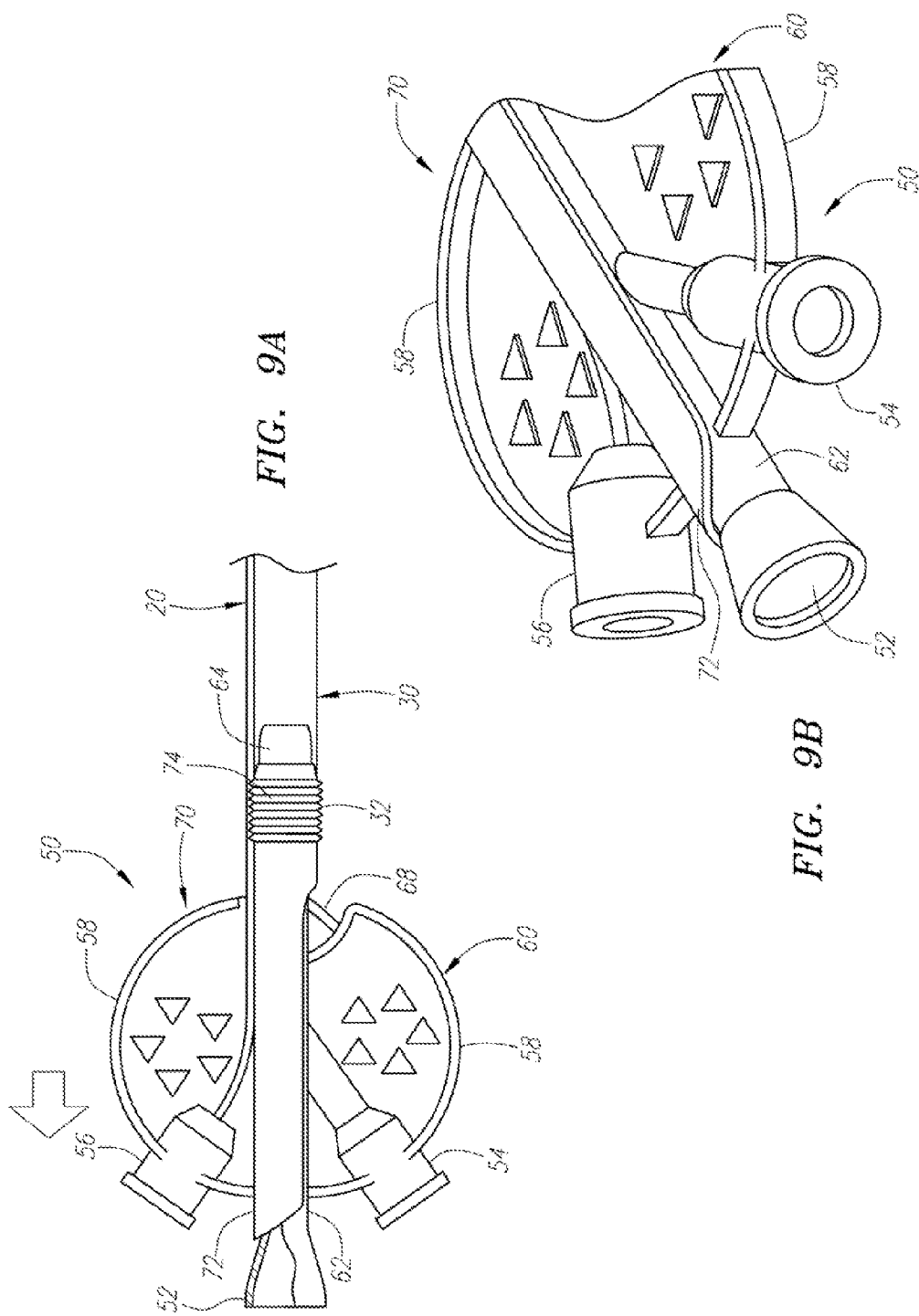

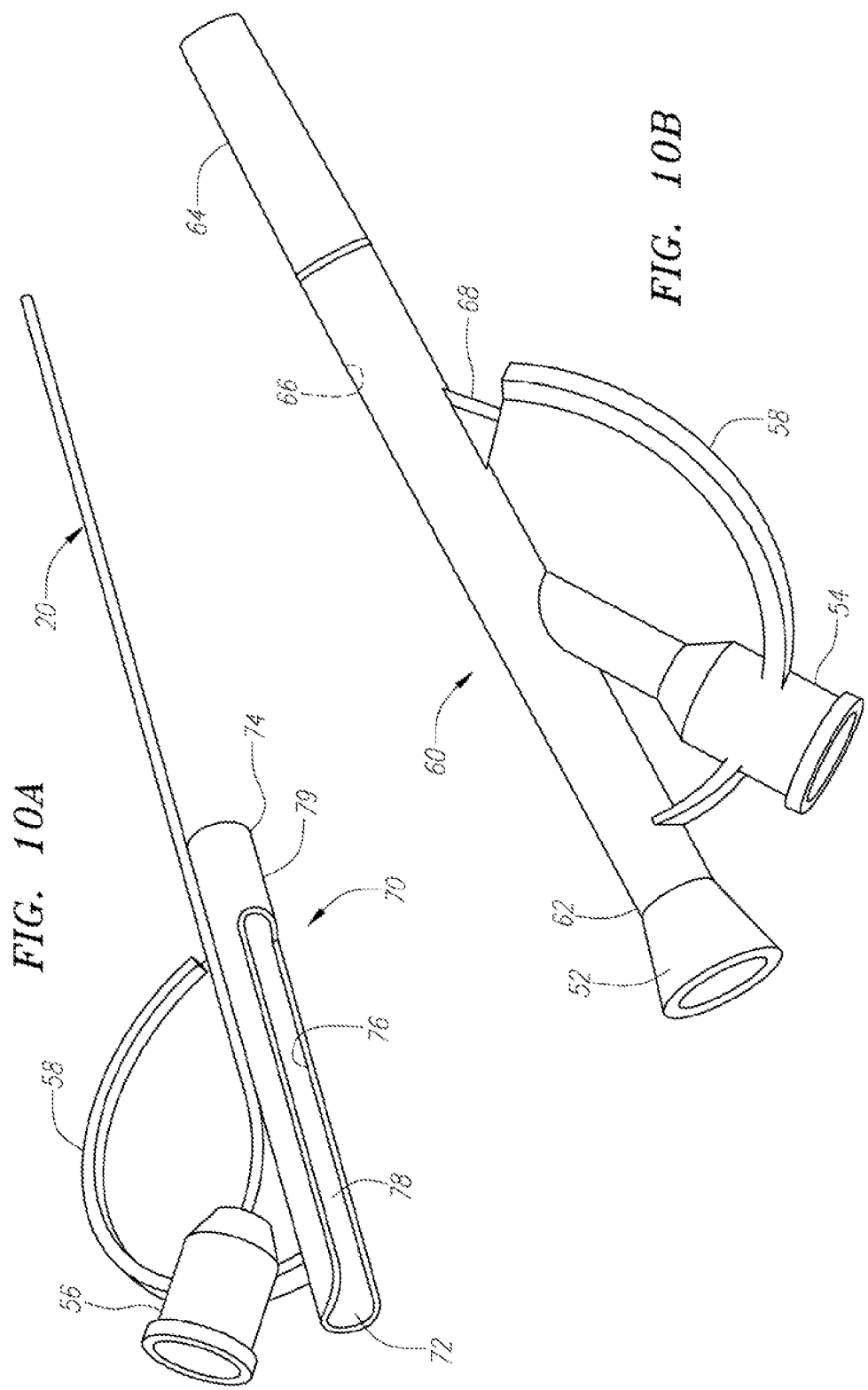

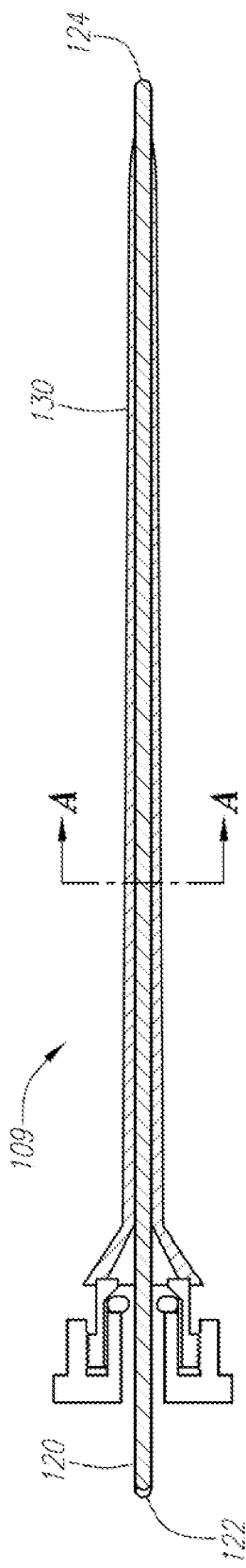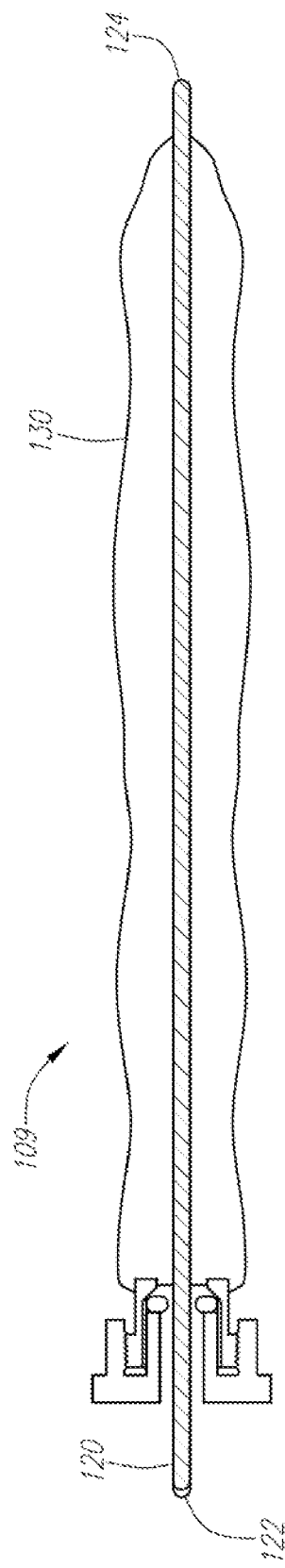
FIG. 24A
FIG. 24B

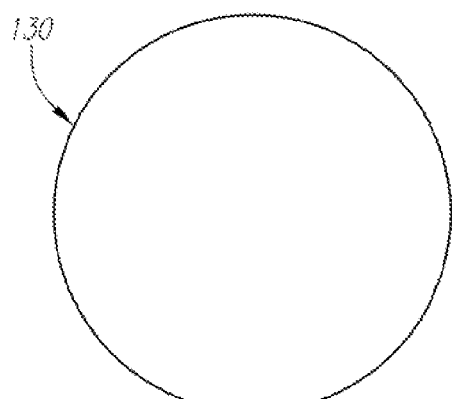
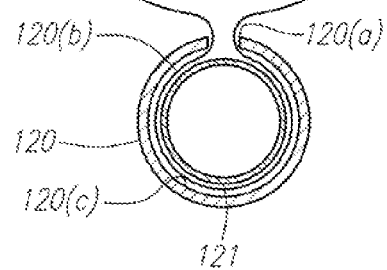
FIG. 25
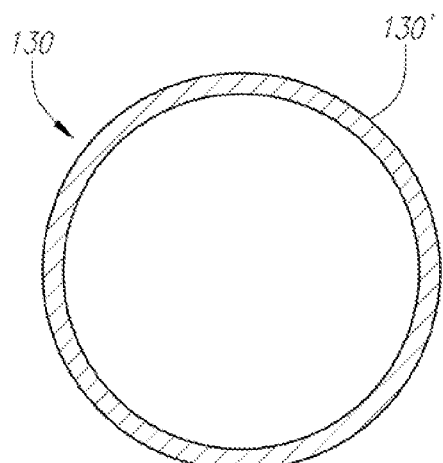
FIG. 26
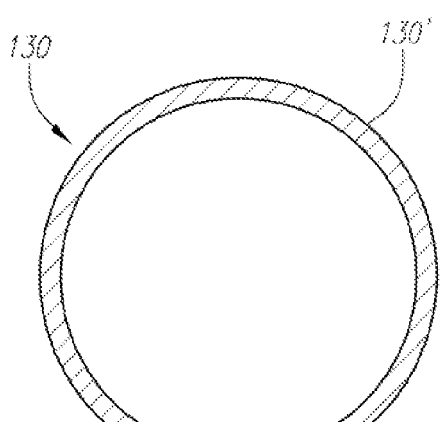
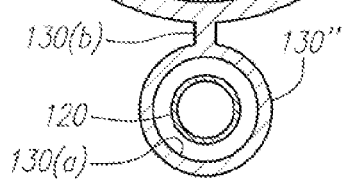
FIG. 27

EXPANDABLE GUIDE SHEATH AND APPARATUS AND METHODS FOR MAKING THEM

This application is a continuation of U.S. application Ser. No. 10/958,034, filed Oct. 4, 2004, now allowed, which claims benefit of provisional application Ser. Nos. 60/508,489, 60/508,490 and 60/508,491, all filed on Oct. 3, 2003, and of provisional application Ser. No. 60/551,901, filed on Mar. 9, 2004. The entire disclosure of these applications are expressly incorporated herein by reference.

FIELD OF THE INVENTION

The present invention relates generally to apparatus and methods for delivering instruments and/or agents during a medical procedure, and, more particularly, to guide sheaths for accessing body lumens and/or delivering instruments into body lumens of a patient, and to methods for making and using them.

BACKGROUND

Minimally invasive procedures have been implemented in a variety of medical settings, e.g., for vascular interventions, such as angioplasty, stenting, embolic protection, electrical heart stimulation, heart mapping and visualization, and the like. These procedures generally rely on accurately navigating and placing instruments within a patient's vasculature.

During such procedures, a target vessel may be accessed using a guidewire advanced through the intervening vasculature into the target vessel, thereby providing a "railway" to the vessel. One or more instruments, e.g., catheters, sheaths, and the like, may be advanced over the guidewire or "rail" into the vessel. Thus, a diagnostic and/or therapeutic procedure may be performed by advancing one or more instruments over this railway.

There are many risks involved with advancing instruments over a guidewire. For example, a catheter or other instrument may skive or otherwise damage a wall of a vessel, particularly as the instrument passes through narrow passages or tortuous anatomy involving sharp bends. Such instruments also risk dislodging embolic material or even perforating the vessel wall.

In addition, it is often desirable to access very small vessels deep within the body, e.g., within a patient's heart, for example, to place a ventricular pacing lead within a coronary vein. However, the instrument(s), e.g., guide sheath, lead, etc., may have a relatively large cross-section and/or may have a relatively blunt distal tip, making it difficult to advance such instruments as deeply as desired into such small vessels.

Accordingly, apparatus and methods for delivering instruments into blood vessels or other body lumens and/or for otherwise accessing vessels or other body lumens would be useful.

SUMMARY OF THE INVENTION

The present invention is directed generally to apparatus and methods for providing access to body lumens and/or for delivering instruments and/or agents into body lumens during a medical procedure. More particularly, the present invention is directed to guide sheaths and methods for making and using such sheaths to facilitate delivering instruments and/or agents into body lumens of a patient, e.g., within the patient's coronary, neuro, and/or peripheral vasculature, within the patient's gastrointestinal tract, urogenital tract, respiratory tract, lymphatic system, and/or within surgically created passages.

In accordance with one embodiment of the invention, an apparatus is provided for accessing a body lumen that includes a tubular proximal portion, and an expandable distal portion. In one embodiment, the proximal portion may include a proximal end, a distal end sized for insertion into a body lumen, and a lumen extending between the proximal and distal ends. The distal portion may include an elongate pushable and/or stiffening member extending from the distal end of the tubular member, and an expandable sheath that is expandable from a contracted condition to minimize a profile of the sheath to allow insertion along with the elongate member into a body lumen, and an enlarged condition wherein the sheath at least partially defines a lumen communicating with the tubular member lumen.

In accordance with another embodiment, a method is provided for accessing a body lumen using an apparatus including a tubular proximal portion and an expandable distal portion having a size smaller than the proximal portion. The distal portion is advanced into a patient's body, e.g., vasculature, with an expandable sheath thereon in a contracted condition. The proximal portion has sufficient length such that a distal end of the proximal portion may reach a first location within the patient's body, e.g., including relatively large body lumens, passages, or chambers, such as the vena cava, right atrium, and/or coronary sinus. With the proximal portion reaching the first location, the distal portion may extend into relatively smaller body lumens, such as the coronary veins, to a target location that is to be accessed. The expandable sheath may be expanded, thereby providing a substantially continuous lumen through the proximal and distal portions to the target location.

In one embodiment, a cardiac pacing lead may be advanced through the proximal portion and the expandable sheath to deliver the lead to the target location. Because such a lead may be floppy, the proximal portion may guide the lead through the relatively large body lumens, passages, or chambers, while the expandable sheath may guide the lead through relatively small and/or tortuous body lumens to the target location. Once the lead is delivered to the target location, the apparatus may be removed.

In accordance with yet another embodiment, an apparatus is provided for accessing a body lumen that includes an expandable tubular member including a proximal end, a distal end sized for insertion into a body lumen, and a side wall. The side wall defines an outer lumen extending between the proximal and distal ends and an inner lumen extending between the proximal and distal ends, the inner lumen at least partially floating within the outer lumen. An elongate stiffening member may be disposed within the inner lumen and may extend between the proximal and distal ends of the expandable tubular member. The elongate member may be attached to or free within the inner lumen.

In one embodiment, the side wall includes a sheet or film having first and second side edges rolled into a tubular shape. The sheet may be attached to itself adjacent the side edges to define the outer lumen, such that the side edges extend into the outer lumen to at least partially define the inner lumen. For example, the first and second side edges may be attached to one another to define the inner lumen.

In addition or alternatively, an inner surface of the outer lumen may include lubricious material. Optionally, a third lumen may be provided within the outer lumen, for example, by attaching a sheet or film to the side wall.

In accordance with still another embodiment, a method is provided for making an expandable sheath using a film having first and second ends, and first and second side edges. The film includes a first lubricious layer and a second layer. In an exemplary embodiment, the first layer may include PTFE or ePTFE, and the second layer may include FEP.

The film may be rolled such that the first and second side edges are adjacent one another to define a lumen such that the second layer is inside the lumen and the first layer is outside the lumen. The second layer may be bonded to itself at or near the first and second side edges. The film may then be inverted such that the second layer is outside the lumen and the first layer is inside the lumen, thereby providing a tubular member having a lubricious material within the lumen.

In one embodiment, after the film is rolled, the second layer may be bonded to itself along a plurality of seams extending between the first and second ends of the film to define first and second lumens adjacent one another. The film may be inverted through the first lumen such that the second lumen is located within the first lumen. Thus, the second lumen may extend from a wall of the outer lumen, thereby coupling the second lumen at least partially to the first lumen, while allowing the second lumen to float within the first lumen.

Optionally, an elongate stiffening and/or pushable member may be attached to or otherwise received within the second lumen. Thus, the elongate member may at least partially float within the first lumen.

In accordance with yet another embodiment, a method for accessing a body lumen of a patient using an apparatus that includes an expandable sheath including an outer lumen and an inner lumen at least partially floating within the outer lumen, and an elongate stiffening and/or pushable member within the inner lumen. The elongate member may be introduced into a body lumen with the expandable sheath in a contracted condition, e.g., by pushing a proximal end of the elongate member.

Once a distal end of the sheath attains a target location, the expandable sheath may be expanded to an enlarged condition such that the outer lumen extends through the body lumen to the target location. One or more instruments, e.g., a cardiac pacing lead, may be advanced through the outer lumen of the expandable sheath into the target location. Because the inner lumen, and consequently, the elongate member, are at least partially floating within the outer lumen, the stiffening member may move relative to the outer lumen as the expandable sheath extends through tortuous anatomy, thereby reducing the risk of the expandable sheath kinking or buckling. After the one or more instruments are delivered into the target location, the apparatus may be removed.

In accordance with still another embodiment, a handle apparatus is provided that includes an outer member including proximal and distal ends, and a lumen extending therebetween, an elongate tubular member extending from the distal end of the outer member, and an inner member connectable to the outer member. The handle apparatus may also include a cutting element, e.g., detachably or permanently attached to the inner member. The inner member may include a lumen for receiving one or more instruments therethrough for delivering the instrument(s) into the tubular member extending from the outer member.

In one embodiment, the cutting element is coupled to the inner member such that, when the outer member is withdrawn proximally relative to the inner member, the cutting element may cut through the tubular member to allow the tubular member to be removed around the inner member. If an instrument is disposed through the inner member, the instrument may remain in place while the outer member and tubular member are removed.

In accordance with yet another embodiment, a method is provided for delivering an instrument into a branch body lumen from a main body lumen within a patient's body. A distal portion of a sheath apparatus may be advanced into the patient's body until a distal end of the sheath apparatus is disposed in the main body lumen adjacent the branch body lumen. An occlusion member on the distal end of the sheath apparatus may be expanded within the main body lumen. An instrument, e.g., a cardiac lead, may be introduced into the sheath apparatus, the instrument passing through an expandable sheath on the sheath apparatus until a distal end of the instrument is adjacent the occlusion member. The instrument may be advanced further, the occlusion member at least partially directing the distal end of the instrument into the branch body lumen.

For example, in one embodiment, the occlusion member may be expanded within the main body lumen distal to the branch body lumen, and the instrument may be advanced until the distal end of the instrument exits an outlet of the expandable sheath and is exposed within the main body lumen. The instrument may be advanced further such that the exposed distal end contacts the occlusion member, the occlusion member deflecting the instrument into the branch body lumen. Alternatively, the occlusion member may include a passage therein communicating with the expandable sheath, and the instrument may be advanced through the passage until the instrument exits transversely from the occlusion member into the branch body lumen.

In accordance with still another embodiment, a sleeve is provided that may be delivered within a coronary sinus of a patient's heart. In one embodiment, the sleeve may include a tubular section and one or more stent-like structures, e.g., on one or both ends of the tubular section. The sleeve may be carried on a cardiac lead or other instrument being delivered through the coronary sinus or on a sheath or other delivery apparatus used for delivering the instrument.

During use, the sleeve may be delivered within the coronary sinus, e.g., while delivering the instrument through the coronary sinus. For example, the instrument may be a cardiac lead that is delivered into a coronary vein accessed via the coronary sinus.

Other aspects and features of the present invention will become apparent from consideration of the following description taken in conjunction with the accompanying drawings.

BRIEF DESCRIPTION OF THE DRAWINGS

FIG. 1A is a perspective view of a first embodiment of a sheath apparatus, including a tubular proximal portion and an expandable distal portion.

FIG. 1B is a perspective detail of an intermediate portion of the apparatus of FIG. 1.

FIG. 3 is a side view of a distal end of the apparatus of FIG. 1.

FIG. 6 is a side view of another embodiment of a sheath apparatus, including a tubular proximal portion and an expandable distal portion.

FIGS. 6A-6C are cross-sections of the apparatus of FIG. 6, taken along lines 6A-6A, 6B-6B, and 6C-6C, respectively.

FIGS. 9A and 9B are side and perspective views, respectively, of a handle apparatus that may be provided on a proximal end of a sheath apparatus.

FIGS. 10A and 10B are perspective views of inner and outer members of the handle apparatus of FIG. 9, respectively.

FIGS. 24A and 24B are side views of another embodiment of a sheath apparatus including a stiffening member and an expandable sheath carried by the stiffening member in collapsed and expanded conditions, respectively.

FIGS. 25-29 are cross-sectional views of alternative embodiments of the sheath apparatus of FIGS. 24A and 24B.

DETAILED DESCRIPTION OF THE PREFERRED EMBODIMENTS

Figure 2:
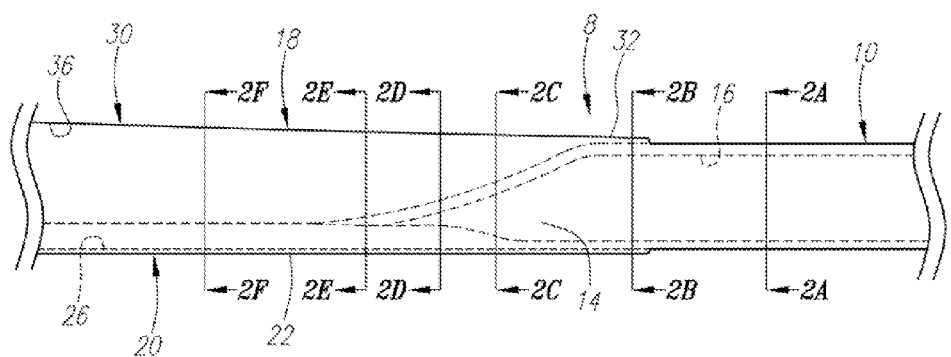
FIG. 2 is a side view of an intermediate portion of the apparatus of FIGS. 1A and 1B.
Figure 2A:
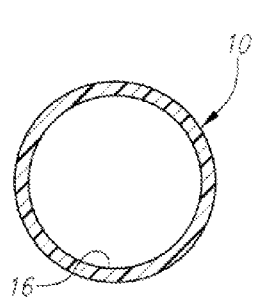
FIGS. 2A-2F are cross-sections of the apparatus of FIG. 2, taken along lines 2A-2A to 2F-2F, respectively.

Turning to the drawings, FIGS. 1A and 1B show a first embodiment of an apparatus 8 for providing access within a body lumen (not shown) and/or for delivering one or more instruments (also not shown) within a body lumen, such as a vessel within a patient's vasculature, a passage within a patient's gastrointestinal tract, urogenital tract, respiratory tract, lymphatic system, and the like.

Generally, the apparatus 8 includes a tubular proximal portion 10 and an expandable distal portion 18. The tubular proximal portion 10 is an elongate tubular member, e.g., a catheter, sheath, and the like, including a proximal end 12, a distal end 14 sized for insertion into a body lumen, and a lumen 16 extending between the proximal and distal ends 12, 14. Optionally, the tubular proximal portion 10 may include one or more additional lumens (not shown), e.g., for receiving a guide wire, inflation media, and/or for perfusion, as described further below. Such additional lumens may be disposed concentrically around one another or in a side-by-side arrangement.

The wall of the tubular portion 10 may be sufficiently thick such that the diameter (or other peripheral dimension) of the tubular portion 10 remains substantially fixed during use of the apparatus 8. The wall of the tubular portion 10 may be rigid or flexible, although self-supporting such that the tubular portion 10 does not collapse on itself. The tubular portion 10 may be sufficiently flexible to allow the tubular portion 10 to bend or otherwise be advanced through a patient's vasculature, while minimizing the risk of kinking or buckling.

The tubular portion 10 may be formed from uniform or variable flexibility material along its length between the proximal and distal ends 12, 14, as desired. For example, it may be desirable for the proximal end 12 to be substantially rigid or semi-rigid, e.g., to facilitate pushing the apparatus 8, while the distal end 14 may be semi-rigid or substantially flexible to accommodate advancement through bends within a patient's vasculature.

The tubular portion 10 may be formed from a variety of materials, such as PTFE, FEP, PFA, PE, Polyamides (Nylon), Polyimide, Pebax, Urethane, and the like. Optionally, the tubular portion 10 may include one or more braids or coils, e.g., embedded within the wall, to provide reinforcement for the tubular portion. In exemplary embodiments, the tubular portion 10 may have a diameter between about half and five millimeters (0.5-5 mm), a wall thickness between about 0.02 and one millimeters (0.02-1.0 mm) (cross-sectional configurations, i.e. multi-lumen cross-sections, and the like may cause wall thicknesses to vary), and a length between about ten and one hundred ten centimeters (10-110 cm). For example, if a subclavian approach is to be used, the proximal portion 10 may have a length of about thirty centimeters (30 cm) or less, while if a femoral approach is to be used, the proximal portion 10 may have a length of about one hundred ten centimeters (110 cm) or more. In one embodiment, the tubular portion 10 may have a length sufficient to reach the vena cava, the right atrium, or the coronary sinus of a patient's heart from a percutaneous entry location, such as a subclavian vein, as described further below.

With continued reference to FIGS. 1A and 1B, the expandable distal portion 18 generally includes an elongate stiffening member 20 providing a "backbone" for the distal portion 18 and an expandable sheath 30. The stiffening member 18 and/or expandable sheath 30 may be attached to or otherwise extend distally from the distal end 14 of the tubular portion 10, as described further below. The stiffening member 20 facilitates advancing the expandable sheath 30 through one or more body lumens, e.g., through a patient's vasculature. The distal portion 18 may be similar in construction and use as the apparatus disclosed in application Ser. No. 10/423,321, filed Apr. 24, 2003, the entire disclosure of which is expressly incorporated by reference herein. In addition or alternatively, the distal portion 18 may be constructed using materials and/or methods similar to any of the embodiments described elsewhere herein.

The stiffening member 20 may be a solid or hollow guidewire, catheter, thread or other filament (e.g., a monofilament), and/or other solid or hollow elongate member. The stiffening member 20 may be sufficiently flexible to facilitate advancement through tortuous anatomy without causing dissection or perforation, yet may have sufficient column strength and/or torque-ability to be "pushable," i.e., such that the stiffening member 20 may be advanced through a body lumen by pushing the proximal end 12 of the tubular portion 10 without substantial risk of kinking and/or buckling. In addition, the stiffening member 20 may also provide sufficient support to facilitate introducing secondary devices, such as a cardiac lead, through the distal portion 18. Cardiac leads or other floppy devices may be difficult to deliver, because of their ability to "prolapse" or double over on themselves in large lumens, like atria, rather than advance to a desired proper location.

In addition, the stiffening member 20 may have sufficient length to be advanced from a first location where the proximal portion 12 terminates, e.g., within the right atrium or coronary sinus of a heart, and a site to be accessed and/or treated, e.g., a coronary vein, as described further below. In exemplary embodiments where the stiffening member 20 is attached to the distal end 14 of the proximal portion 10, the stiffening member 20 may be between about ten and fifty centimeters (10-50 cm), or may be not more than about thirty centimeters (30 cm). Alternatively, the stiffening member 20 may extend proximally the entire length of the proximal portion 10, e.g., within or along the proximal portion 10, and therefore may have additional length corresponding to the length of the proximal portion 10.

As shown in FIGS. 1A-3, the stiffening member 20 may be an elongate member including a proximal end 22, and a distal end 24 having a size and/or shape for insertion into a body lumen. Optionally, the stiffening member 20 may terminate in a rounded or other substantially atraumatic distal tip 28, e.g., a "J" tip, a balloon or other expandable member, and the like, as explained further below. If desired, the distal tip 28 may be shaped to provide steerability and/or directionality, or may include one or more internal elements to provide a steerable distal tip.

Figure 21A:
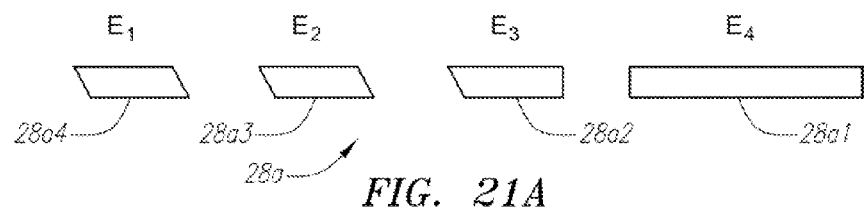
FIGS. 21A, 22A, and 23A are exploded side views of distal tips of a stiffening member having multiple sections providing a variable stiffness for the distal tip.
Figure 21B:
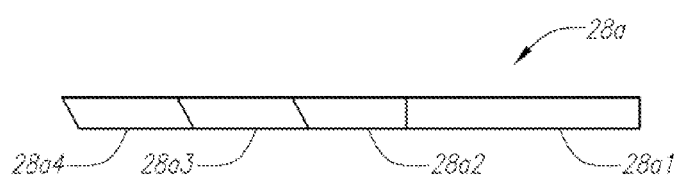
FIGS. 21B, 22B, and 23B are side views of the distal tips of FIGS. 21A, 22A, and 23A, respectively, with the sections assembled together.

Optionally, as shown in FIGS. 21-23, the distal tip 28 may be formed from multiple sections of tubing or other material having different stiffness or modulus of elasticity. For example, as shown in FIGS. 21A and 21B, the distal tip 28a may include a first tubular section 28a1 having a stiffness similar to the adjacent portion of the stiffening member (not shown). Distally adjacent tubular sections 28a2-28a4 may have progressively less stiffness, e.g., such that the distalmost section 28a4 is "floppy" or soft, which may facilitate advancing the distal tip 28a through tortuous anatomy.

Figure 22A:
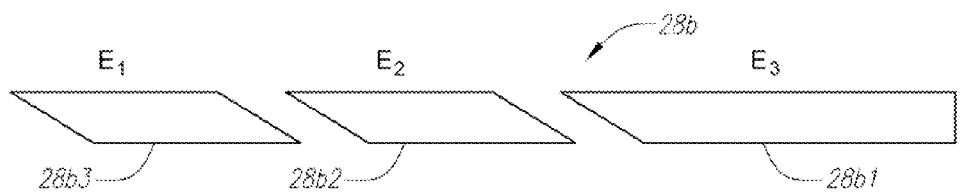
Figure 22B:
Figure 23A:
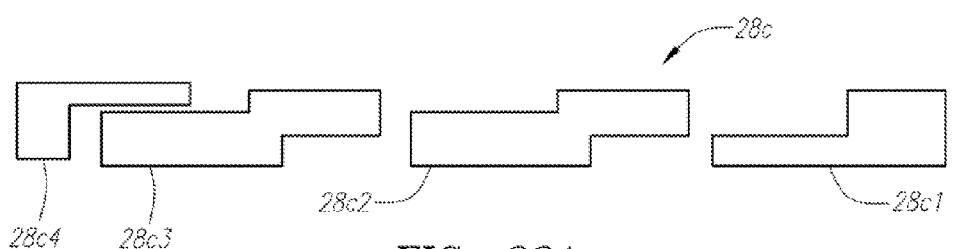
Figure 23B:
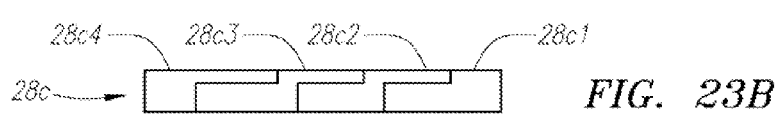

Alternatively, as shown in FIGS. 22A and 22B, sections 28b1-28b3 of the distal tip 28b may be angled on the ends to be attached to one another. This may create a distal tip 28b whose stiffness changes less abruptly. In a further alternative, shown in FIGS. 23A and 23B, the sections 28c1-28c4 may be beveled or otherwise staggered to provide a more gradual and/or continuous change in stiffness along the distal tip 28c.

Optionally, the stiffening member 20 may include one or more lumens 26 extending between the proximal and distal ends 22, 24. For example, in the embodiment of FIGS. 1A and 2, the stiffening member 20 includes a single lumen 26, best seen in FIG. 2F. Alternatively, in the embodiment of FIG. 6, the stiffening member 20' includes two side-by-side lumens 26a,' 26b,' best seen in FIGS. 6B and 6C. The lumen(s) may be sized to allow fluids to be delivered therethrough and/or to receive a guide wire, catheter, or other instrument (not shown) therethrough.

Figure 2B:
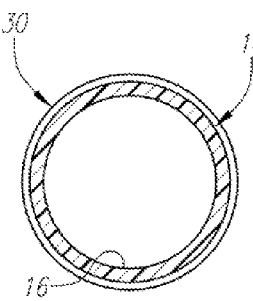
Figure 2C:
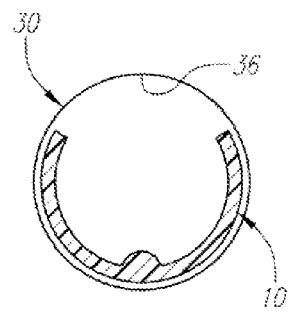
Figure 2D:
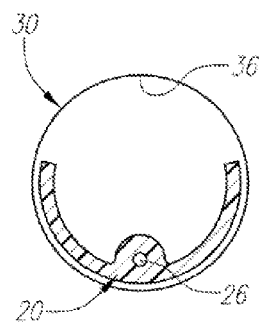
Figure 2E:
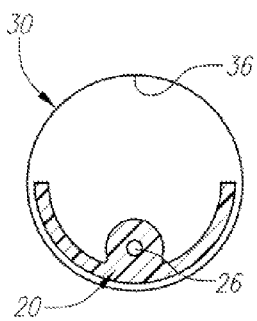
Figure 2F:
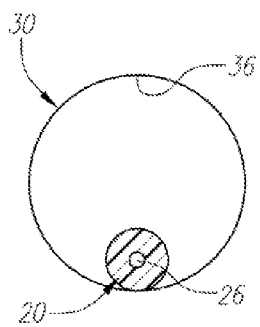

As shown in FIG. 2F, the stiffening member 20 may have a cylindrical or other substantially symmetrical cross-section, e.g., including a single lumen 26. Alternatively, as shown in FIGS. 6B and 6C, the stiffening member 20' may have an asymmetrical cross-section, e.g., including a plurality of lumens 26a,' 26b.' In other embodiments, the stiffening member may have an arcuate cross-section (not shown), such as those disclosed in application Ser. No. 10/432,321, incorporated by reference above. The diameter or other cross-section of the stiffening member 20 is substantially smaller than that of the tubular proximal portion 10, e.g., between about 0.05-5 millimeters, or between about 0.2-2 millimeters.

Optionally, as best seen in FIG. 3, the stiffening member 20 may include a balloon or other expandable occlusion member 27 on the distal end 24. If a balloon 27 is provided, the stiffening member 20 may include an inflation lumen (not shown) that extends through the stiffening member 20 from the proximal end 12 (see FIG. 1A) to communicate with an interior of the balloon 27. A source of inflation media, e.g., a syringe of saline (not shown) may be coupled to port 56 (see FIG. 1A) that may communicate with the inflation lumen. Exemplary occlusion members that may be provided and methods for using them are disclosed in co-pending application Ser. No. 10/934,082, filed Sep. 2, 2004, the entire disclosure of which is expressly incorporated by reference herein.

In addition or alternatively, the stiffening member 20 may include one or more outlet ports 29 on the distal end 24, e.g., distal to the balloon 27, as shown in FIG. 3, or proximal to the balloon 27 (not shown). As shown in FIGS. 6-6C, if the stiffening member 20' includes a balloon 27' and one or more outlet ports 29,' the stiffening member 20' may include two lumens 26a,' 26b' communicating with the interior of the balloon 27' and the outlet ports, respectively.

The stiffening member 20 may be formed from a variety of materials and using various methods. For example, the stiffening member 20 may be formed from plastic, glass, metal, or composites of such materials using known methods, such as extrusion and the like, thereby providing a desired combination of flexibility and column strength. In exemplary embodiments, the stiffening member 20 may be formed from one or more of polyimide, polyamide (nylon)), Ultem, PEEK, Nitinol, and optionally, may include braid and/or coil reinforcing polymers, similar to other components described herein.

Turning to FIGS. 1B and 2, a transition may be provided between the distal end 14 of the tubular portion 10 and the proximal end 22 of the stiffening member 20. As shown, the distal end 14 of the tubular portion 10 may be beveled or otherwise tapered, e.g., by molding-in the tapered shape or by cutting or otherwise removing a section of the distal end 14. Such a shape may facilitate advancing the tubular portion 10 into a body lumen within which the smaller stiffening member 20 has been previously introduced, as described further below.

Figure 20:
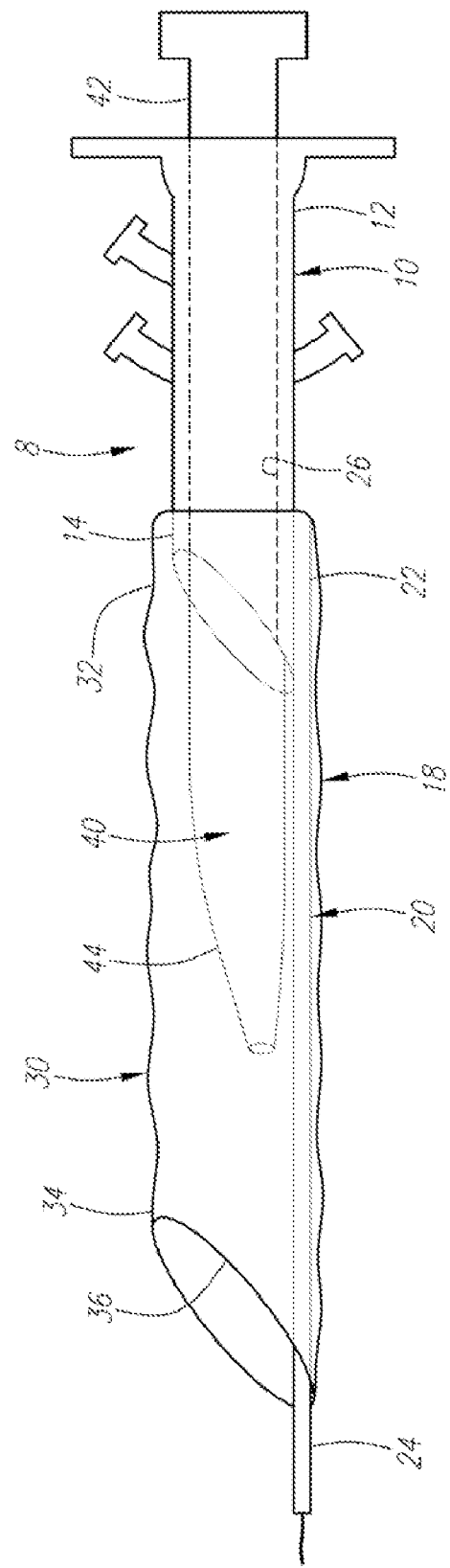
FIG. 20 is a side view of the apparatus of FIGS. 1A and 1B, having an obturator inserted therein for providing a transition between the proximal and distal portions of the apparatus.

In addition or alternatively, as shown in FIG. 20, an obturator 40 may be provided that includes a proximal end 42, and a tapered and/or rounded distal end 44 sized to be slidably inserted into the lumen 26 of the tubular portion 10. The obturator 40 may have a length corresponding to a length of the tubular portion 10 such that the distal end 44 of the obturator 40 extends partially into the expandable distal portion 18 when the obturator 40 is fully advanced into the tubular portion 10. The distal end 44 of the obturator 40 may be relatively flexible and/or soft to provide an atraumatic transition between the tubular proximal portion 10 and the expandable distal portion 18.

Returning to FIGS. 1B and 2, the proximal end 22 of the stiffening member 20 may be attached to the distal end 14 of the tubular portion 10, e.g., such that the stiffening member extends axially and/or tangentially from the wall of the tubular portion 10. The stiffening member 20 may be attached to the tubular portion 10, e.g., by one or more of chemical bonding, thermal bonding, sonic welding, interference fit, and/or one or more cooperating connectors. Alternatively, the tubular portion 10 and stiffening member 20 may be formed as a single piece, e.g., by extrusion, injection molding, and the like.

With additional reference to FIGS. 1A-3, the expandable sheath 30 generally includes a proximal end 32, a distal end 34, and one or more side walls extending between the proximal and distal ends 32, 34, thereby at least partially defining a lumen 36. As used herein, the term "sheath" may include any structure that at least partially defines a lumen, whether the structure is substantially tubular or only partially defines the lumen 36.

The sheath 30 may be expandable from a contracted condition (not shown) to an enlarged condition, as shown in FIG. 1A. When the sheath 30 is in the contracted condition, the distal portion 18 may assume a low profile to facilitate insertion into a body lumen (not shown). To place the sheath 30 in the contracted condition, the sheath 30 may be folded, twisted, wrapped, or otherwise compressed around or adjacent to the stiffening member 20 (e.g., using an internal vacuum with the lumen 36 of the sheath 30 and/or an external force). In another embodiment, the sheath 30 may be left unconstrained. The "limpness" of the sheath 30 may allow the sheath material to readily deflect when the sheath 30 contacts any bodily structures, such that the sheath 30 may perform as if it were maintained in a collapsed configuration, when it is not actually constrained.

Optionally, the sheath 30 may be secured in the contracted condition, e.g., using a constraint (not shown), such as a sheath, tether, or releasable adhesive or bonding material at one or more locations or continuously along the sheath 30. Alternatively, the sheath 30 may simply maintain the contracted condition until an external force, e.g., fluid or an instrument, are delivered therein to expand the sheath 30 towards the enlarged condition. Exemplary apparatus and methods for placing and/or maintaining the sheath 30 in the contracted condition are disclosed in application Ser. No. 10/423,321, incorporated by reference above. In the enlarged condition, the sheath 30 may unfold, untwist, unwrap, or otherwise expand to at least partially define the lumen 36, e.g., for receiving a fluid (e.g., a medicament, anti-thrombotic agent, and the like) and/or one or more instruments therethrough (not shown).

Because the sheath 30 is relatively thin-walled, the distal portion 18 may attain a relatively low profile when the sheath 30 is in the contracted condition compared to the proximal portion 10. For example, with the sheath 30 in the contracted condition, the distal portion 18 may have a maximum diameter between about 0.1 and about ten millimeters (0.1-10 mm), or between about 0.2 and about three millimeters (0.2-3 mm). Conversely, a relatively large lumen 36 may be provided when the sheath 30 is expanded to the enlarged condition, e.g., having a diameter or other maximum cross-section between about 0.3 and about one hundred millimeters (0.3-100 mm), or preferably between about 0.3 and about twenty millimeters (0.3-20 mm).

The sheath 30 may be formed from relatively thin, flexible material, as compared to the stiffening member 20 and/or tubular proximal portion 10. Thus, the sheath 30 may be "flimsy," i.e., may have little or no rigidity such that the sheath 30 provides little resistance to expansion and/or contraction, and/or may conform substantially to anatomy within which it is deployed. As used herein, "flimsy" means that the material of the sheath 30 is not biased to assume any particular configuration or shape, and therefore, the sheath 30 may adopt whatever shape and/or configuration that is imposed upon it, e.g., by being folded or otherwise compressed, by being subjected to external or internal pressure or force, and the like. To achieve this, the sheath 30 may have a relatively thin wall thickness, e.g., between about 0.001-1.25 millimeters, or between about 0.005-0.06 millimeter.

The sheath 30 may be constructed of one or more materials that may be fabricated to a relatively thin, flexible configuration, e.g., polytetrafluoroethylene (PTFE), expanded polytetrafluoroethylene (ePTFE), fluorinated ethylenepropylene (FEP), polyethylene teraphathalate (PET), urethane, olefins, polyethylene (PE), silicone, latex, isoprene, chronoprene; and the like. The sheath 30 may be formed from lubricious material and/or may be coated, e.g., with silicone or other coating, e.g., for facilitating inserting one or more instruments (not shown) through the lumen 36.

In some embodiments, it may be desirable that the internal surface of the sheath 30 be lubricious to allow for smooth passage of an instrument, such as an electrical pacing lead (not shown), therethrough. This may be accomplished by forming the sheath 30 out of a lubricious material such as, a hydrophobic fluoropolymer. Alternatively, the sheath 30 may be formed from material that has been surface-treated and/or coated with a hydrophilic coating material. If it is particularly difficult to treat or coat the interior surface of the sheath 30, the treatment or coating material may be applied to the exterior surface of the sheath 30. The sheath 30 may then be inverted or "everted," for example, by pulling one end of the sheath 30 through the sheath lumen to place the exterior treated/coated surface on the interior of the sheath 30 (i.e., turn the sheath 30 inside-out).

The sheath 30 may be formed from thin-walled polymeric tubing or a thin polymeric film. With respect to tube-based structures, the tubing may be extruded (or co-extruded if multiple lumens are used as is described in more detail below) to a thin wall. Alternatively, one or more post-processing steps, such as blow molding, stretching, or drawing tube through a heated die may be used to form the thin walled sheath 30. In still another embodiment, a thin film may be produced and rolled into a tubular configuration. In this embodiment, the thin film may be surface-treated and/or coated before being rolled into the tubular configuration.

With respect to thin film-based structures, a seam may be formed along all or a portion of the length of the sheath 30. The seam may be formed from any number of methods, for example, chemical bonding with adhesives, heat sealing, ultrasonic welding, laser welding, or mechanical bonding using stitching or the like.

As described above, in one embodiment, the sheath 30 may be formed from a lubricious fluoropolymer. For example, a thin-walled sheath 30 may be formed by rolling a cast thin film formed from PTFE having a layer of FEP formed thereon into a tubular structure. The FEP may then be sealed (for example, by heat sealing) to form the final tubular structure.

The PTFE layer is preferably disposed on the interior surface of the sheath 30 since PTFE is more lubricious than FEP.

In still another alternative embodiment, the sheath 30 may be formed from ePTFE manufactured into a thin-walled tube (or multiple tubes) or thin film. Additional lumens may also be formed within the sheath 30. For example, these additional lumens may be used to house the backbone (i.e., elongate stiffening member 20) or used to inject contrast for imaging and/or perfusing blood or other fluids. As one example, additional lumens may be formed by joining un-sintered PTFE or ePTFE tube structures, which may then be heat-sealed along their lengths, followed by a sintering process.

In one embodiment, the sheath 30 is formed from substantially inelastic material, i.e., such that a primary contribution to the sheath 30 expanding and contracting is unfolding or folding the material of the sheath 30. Alternatively, the sheath 30 may be formed from an elastic material such that a secondary contribution to the sheath 30 expanding and contracting is an elasticity of the material of the sheath 30, i.e., such that a circumference or other peripheral dimension of the sheath 30 may increase as the sheath 30 expands towards the enlarged condition.

The sheath 30 may be substantially nonporous. Alternatively, the sheath 30 may be porous, for example, substantially continuously along its length or at one or more locations, e.g., to allow fluid delivered into the lumen 36 to pass through the wall of the sheath 30 in a desired manner, e.g., to deliver fluid to a wall of a vessel (not shown) through which the sheath 30 extends. In a further alternative, the sheath 30 may include one or more discrete openings (not shown) at one or more locations along its length.

In addition or alternatively, the sheath 30 may include a thin mesh, e.g. a perforated urethane film and the like. In a further alternative, the lubricity of the sheath 30 may be enhanced by providing a lubricious coating, lining, ribbing, and the like (not shown), and/or applying a lubricant, e.g., to the interior surface and/or outer surface of the sheath 30. The sheath 30 may include a single layer or multiple layers of such materials, such that a desired flexibility and lubricity is achieved. Thus, the sheath 30 may easily expand and/or line a body lumen to reduce friction and/or accommodate instruments being advanced through the body lumen, as explained further below.

Optionally, the sheath 30 may include one or more reinforcing elements (not shown). For example, a wire, thread, filament, and the like, formed from plastic, glass, metal, or composites of such materials, may be attached to an outer surface, an inner surface, and/or embedded in a wall of the sheath 30. In addition or alternatively, the sheath 30 may include relatively thickened regions that may be formed directly from the wall material. The reinforcing element(s) may extend circumferentially and/or helically around the sheath 30, and/or may extend axially along the sheath 30, depending upon the reinforcement desired. The reinforcement element(s) may also bias the sheath 30 to assume a desired shape or configuration when expanded towards the enlarged condition.

With particular reference to FIGS. 1B and 2, the proximal end 32 of the sheath 30 may be attached to the distal end 14 of the tubular portion 10, e.g., by chemical bonding, thermal bonding, sonic welding, interference fit, and the like. Thus, as shown in FIG. 2B, the sheath 30 may surround and overly the distal end 14 of the tubular portion 10 such that the lumen 16 of the tubular portion 10 communicates with the lumen 36 of the sheath 30. When the sheath 30 is compressed to the contracted condition, the proximal end 32 of the sheath 30 may be compressed against the tapered distal end 14 of the tubular portion 10.

Figure 4:
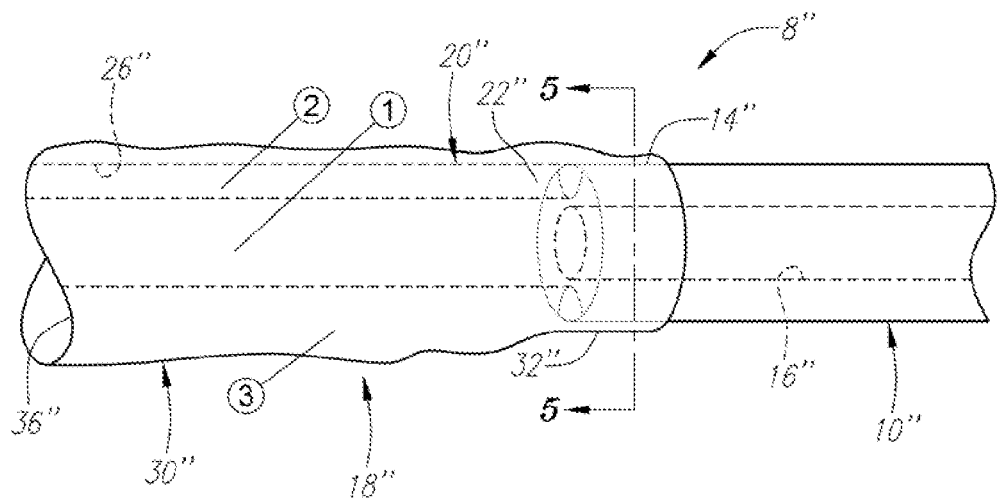
FIG. 4 is a side view of an intermediate portion of an alternative embodiment of a sheath apparatus.
Figure 5:
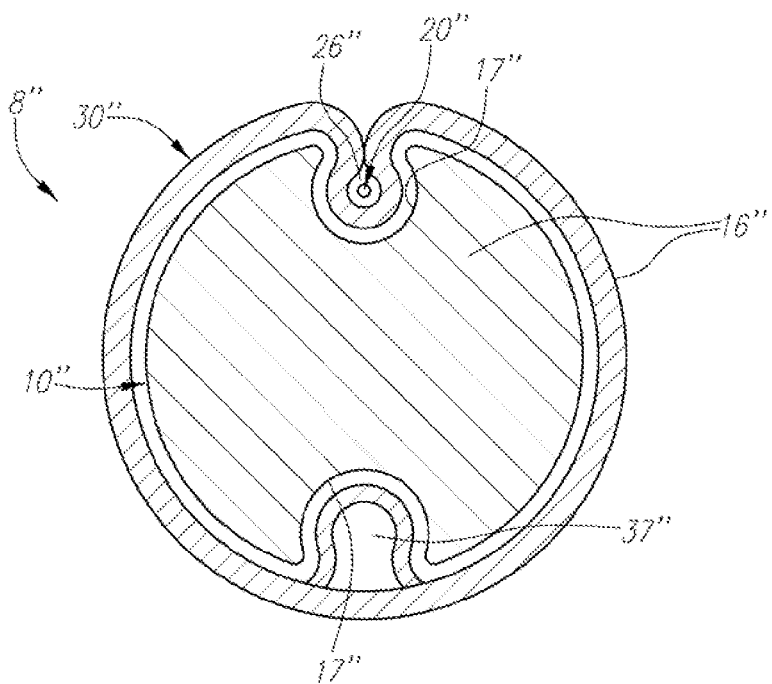
FIG. 5 is a cross-section of the apparatus of FIG. 4, taken along line 5-5.

Turning to FIGS. 4 and 5, an alternative embodiment is shown of an apparatus 8" that includes an expandable distal portion 18" extending distally from a tubular proximal portion 10." As shown, the tubular portion 10" may include a proximal end (not shown), a distal end 14," and one or more lumens extending therebetween. As shown, the tubular portion 10" includes a single lumen 16" and a pair of grooves 17" extending along the outer wall of the tubular portion 10." Alternatively, the grooves 17" may be replaced with one or more additional lumens (not shown), extending along the wall of the tubular portion 10." Unlike the previous embodiment, the distal end 14" may be substantially blunt, although alternatively, the distal end 14" may also be beveled or otherwise tapered, similar to the previous embodiments.

The expandable distal portion 18" may include a stiffening member 20" and an expandable sheath 30," similar to the previous embodiments. The stiffening member 20" may include a proximal end 22" attached to the distal end 14" of the tubular portion 18," e.g., aligned with one of the grooves 17" such that a lumen 26" within the stiffening member 20" communicates with the groove 17." A catheter, other tubular body, or cover (not shown) may be snapped into the groove 17" or otherwise attached to the tubular portion 10" to provide a lumen communicating with the stiffening member 20."

The tubular body or cover may extend at least partially towards the proximal end of the tubular portion 10," e.g., to provide a lumen for receiving a guidewire or other element therethrough. For example, the tubular body may extend entirely to the proximal end of the tubular portion 10" or to an intermediate location, e.g., to provide a rapid exchange lumen.

In addition, as best seen in FIG. 5, the sheath 30" may include a supplemental lumen 37" attached to or otherwise extending along a wall of the sheath 30," e.g., to provide a fluid-tight lumen for delivering contrast media or other fluids beyond the distal end of the sheath 30." The lumen 37" may be aligned with groove 17," which may include a tubular body or cover, similar to the other groove 17."

Returning to FIG. 1A, optionally, a proximal end 12 of the tubular proximal portion 10 may include a handle or other structure 50, e.g., that may facilitate manipulating the apparatus 80 and/or inserting one or more instruments into the lumen 16 of the tubular portion 10. In addition or alternatively, the handle 50 may include one or more valves, e.g., a hemostatic valve 52, that may substantially seal the lumen 16 from proximal flow of fluid, yet accommodate instruments being introduced into the lumen 16. In addition, the handle 50 may include one or more additional ports 54, 56 for communicating with the lumen(s) within stiffening member 20 and/or sheath 30.

Turning to FIGS. 9A-10C, an exemplary embodiment of a handle 50 is shown that includes two portions 60, 70 including wings 58 that may facilitate manipulation and/or stabilization of the handle 50. As shown, the handle 50 includes an inner member 60 and an outer member 70 that are connectable to and/or releasable from one another.

With particular reference to FIG. 10B, the inner member 60 may include a relatively short tubular section, e.g., between two and ten centimeters (2-10 cm) in length, and including a proximal end 62, a tapered distal end 64, and a lumen 66 extending therebetween. The proximal end 62 may include one or more valves, e.g., hemostatic valve 52, that may substantially seal the lumen 66, yet accommodate insertion of one or more instruments (not shown) therein. The inner member 60 may include a side port 54, e.g., including a hemostatic valve, a luer lock or other connector, and the like (not shown), that communicates with the lumen 66. A source of fluid, e.g., a syringe of saline (not shown) may be connected to the side port 54 for flushing or otherwise delivering fluid into the lumen 66 (and consequently into the lumen of the sheath 30 or other apparatus coupled to the handle 50).

Optionally, the inner member 60 may include a blade 68 adjacent the tubular section, e.g., partially embedded or otherwise attached to the outer surface of the tubular section. The blade 68 may provide a slitter for splitting or otherwise cutting the outer member 70, and/or one or more portions of the sheath 30 (or other apparatus coupled to the handle 50), as described further below.

Turning to FIG. 10A, the outer member 70 may include a tubular section including a proximal end 72, a distal end 74, and a lumen 76 extending therebetween. The outer member 70 may have a size such that the inner member 60 may be at least partially received within the lumen 76. Optionally, the outer member 70 may include a slot 78 extending distally from the proximal end 72 that may receive the wing 58 of the inner member 60 to interlock the inner and outer members 60, 70. In addition, the slot 78 may align the blade 68 with a weakened or otherwise easily cut region 79 of the outer member 70. Alternatively, similar to the embodiment shown in FIG. 15A, the outer member 70e may have a "C" shaped cross-section, including a continuous slot 78e extending between the proximal and distal ends 72e, 74e.

Returning to FIG. 10A, a stiffening member 20 may be attached to or otherwise extend distally from the outer member 70. The stiffening member 20 may be substantially permanently attached to the outer member 70, e.g., extending along an exterior surface of the outer member 70, as shown. Alternatively, the stiffening member 20 may be detachable from the outer member 70. The outer member 70 may include a side port 56 that communicates with a lumen (not shown) of the stiffening member 20. The side port 56 may include a seal and/or connector, similar to the side port 54. Alternatively, the stiffening member 20 may be connected to the distal end 74 of the outer member 70, similar to the attachments between the stiffening member 20 and proximal tubular portion 10 described above (e.g., as shown in FIGS. 2 and 4).

An expandable sheath 30 (not shown in FIG. 10A, see FIG. 9A) may be attached to or extend along the stiffening member 20. A proximal end 32 of the expandable sheath 30 may surround or otherwise be attached to the distal end 74 of the outer member 70 (e.g., similar to FIG. 1B or 4). The stiffening member 20 and expandable sheath 30 may be constructed similar to any of the other embodiments described herein. Alternatively, a proximal tubular portion (not shown) may be attached to or otherwise extend from the outer member 70, e.g., similar to the tubular portions described above, and an expandable distal portion (also not shown) may extend from the tubular portion.

Figure 10C:
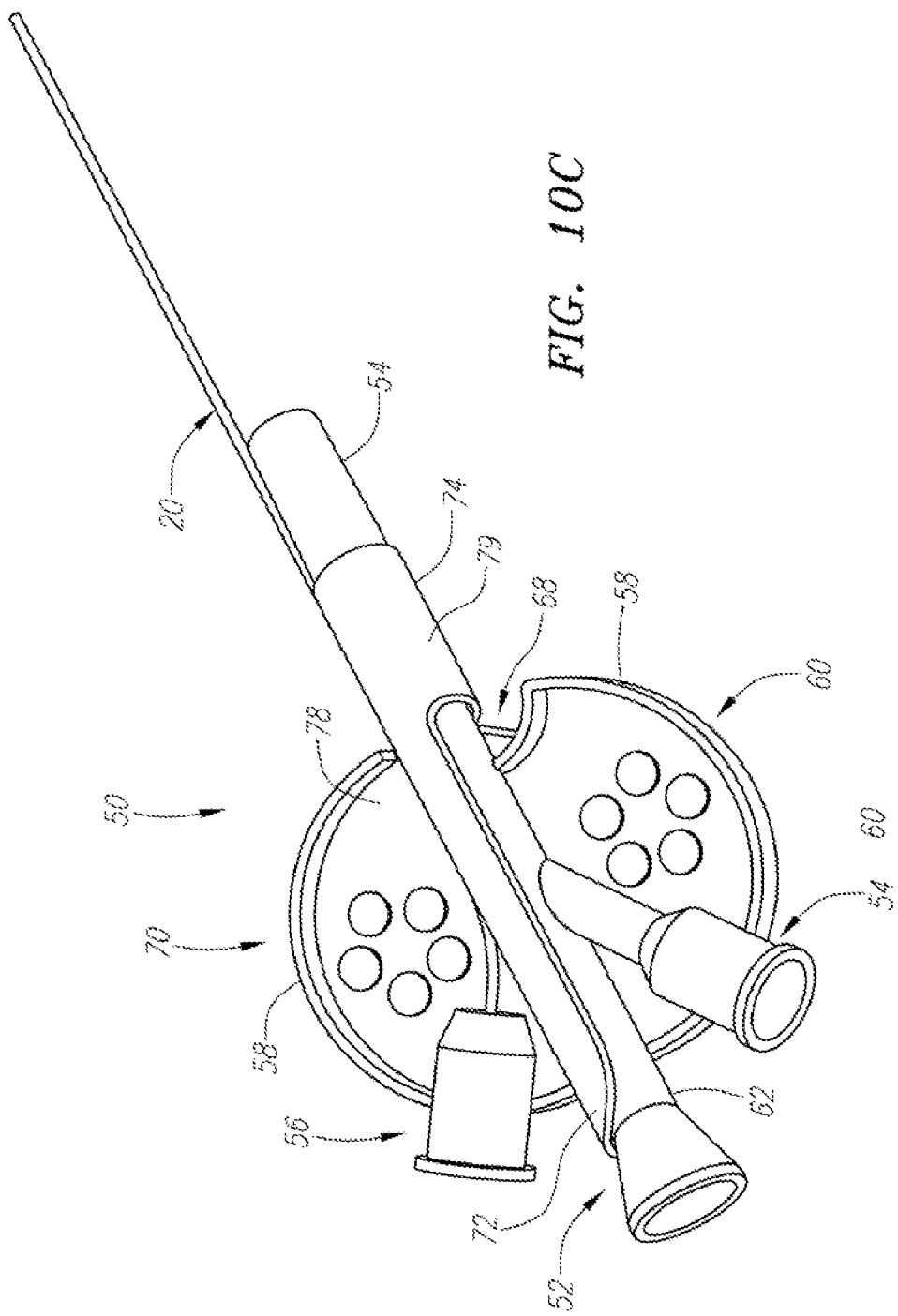
FIG. 10C is a perspective view of the inner and outer members of FIGS. 10A and 10B assembled together.

As shown in FIG. 10C, the distal end 64 of the inner member 60 may be inserted into the lumen 76 from the proximal end 72 of the outer member such that the wing 58 and blade 68 are received within the slot 78 in the outer member 70, thereby assembling the handle 50. As assembled, the distal end 64 of the inner member 60 may extend a short distance beyond the distal end 74 of the outer member 70, e.g., adjacent the stiffening member 20 and/or partially into the expandable sheath 30. Receiving the wing 58 of the inner member 60 in slot 78 may limit relative movement of the inner and outer members 60, 70, e.g., while the handle 50 is being manipulated, separated, and/or while instruments (not shown) are inserted or removed from the inner member 60.

As described further below, when it is desired to remove the stiffening member 20 and expandable sheath 30, the outer member 70 may be withdrawn proximally relative to the inner member 60. This causes the blade 68 to contact the weakened or easily cut region 79 of the outer member 70, e.g., to cut through the outer member 70. As the outer member 70 is withdrawn further, the blade 68 may cut through the expandable sheath 30 (and/or the tubular proximal portion, if present), causing the expandable sheath 30 to split. Thus, the handle 50 may allow the expandable sheath 30 to be removed, while leaving the inner member 60 in place, e.g. with an instrument (not shown) maintained within the lumen 66 of the inner member 60 substantially stationary.

In alternative embodiments, other handles may be provided on the sheath apparatus 8 or any other sheath apparatus described elsewhere herein. In addition, the handle apparatus described herein may be useful for other applications, including introducer sheaths (not shown) for catheter-based procedures, and the like.

Figure 11:
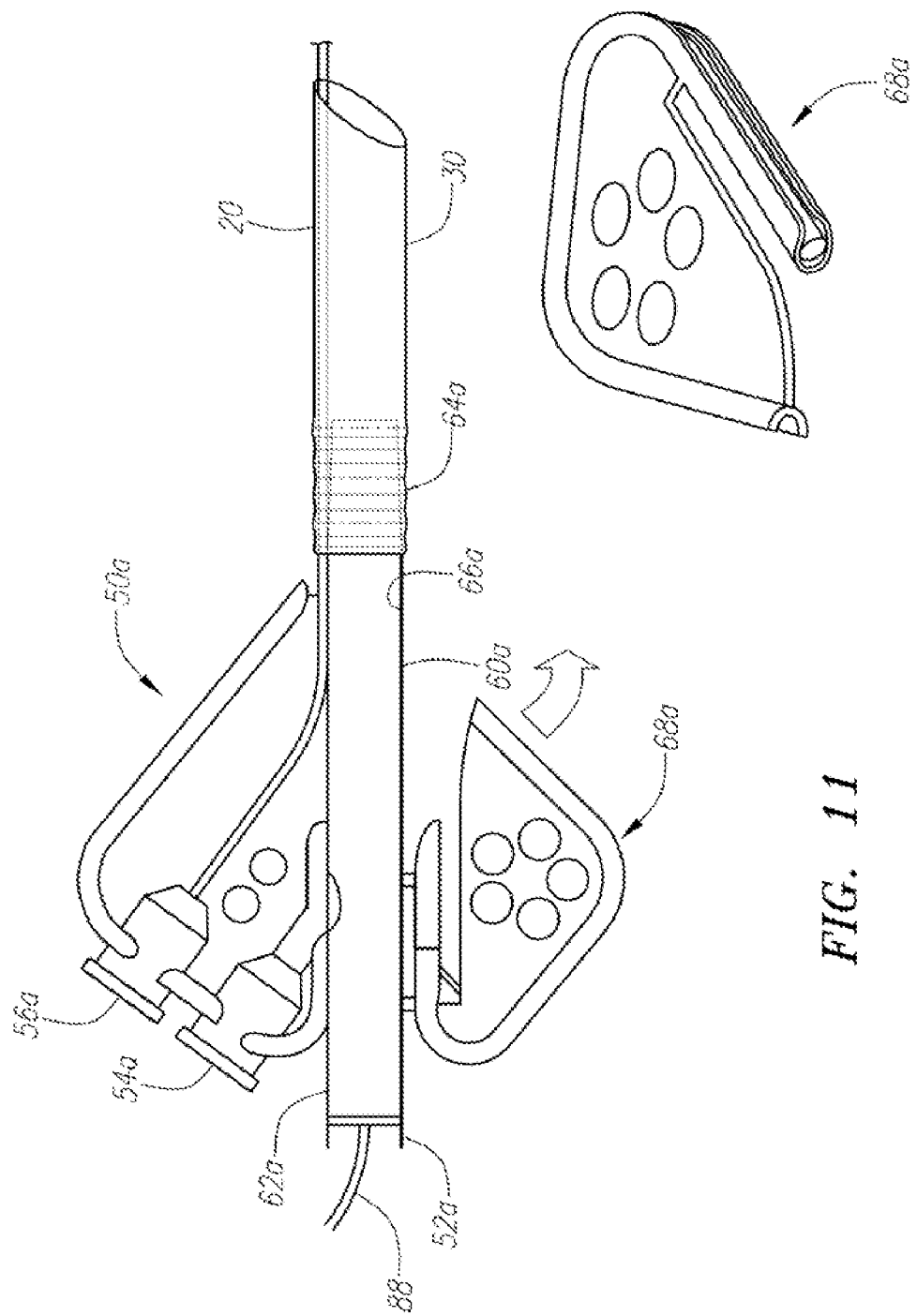
FIG. 11 is a side view of another embodiment of a handle apparatus, including a detachable slitter.

Turning to FIG. 11, a handle 50a is shown that includes a relatively short tubular section 60a, including a proximal end 62a, a distal end 64a, and a lumen 66a extending therebetween. The handle 50a may be a single piece tubular section, or may include multiple sections similar to the previous embodiment. A hemostatic valve 52a may be provided in the proximal end 62a, similar to the previous embodiment, to seal the lumen 66a while accommodating insertion of one or more instruments therein, e.g., guidewire 88. A stiffening member 20 and expandable sheath 30 may extend from the distal end 64a of the tubular section 60a, similar to the previous embodiment. In addition, the handle 50a may include a first side port 54a communicating with the lumen of the tubular section 60a (and consequently, the lumen of the expandable sheath 30), and a second side port 56a communicating with a lumen of the stiffening member 20.

Unlike the previous embodiment, the handle 50a includes a detachable slitter tool 68a that may be attached to the handle 50a, e.g., along the tubular section 60a. The slitter tool 68a may be attached by one or more tabs or other elements that may be broken, e.g., by bending the slitter 68a relative to the tubular section 60a. Once separated, the slitter 68a may be used to split or otherwise cut the tubular section 60a and/or the expandable sheath 30 similar to other embodiments described herein.

Figure 12:
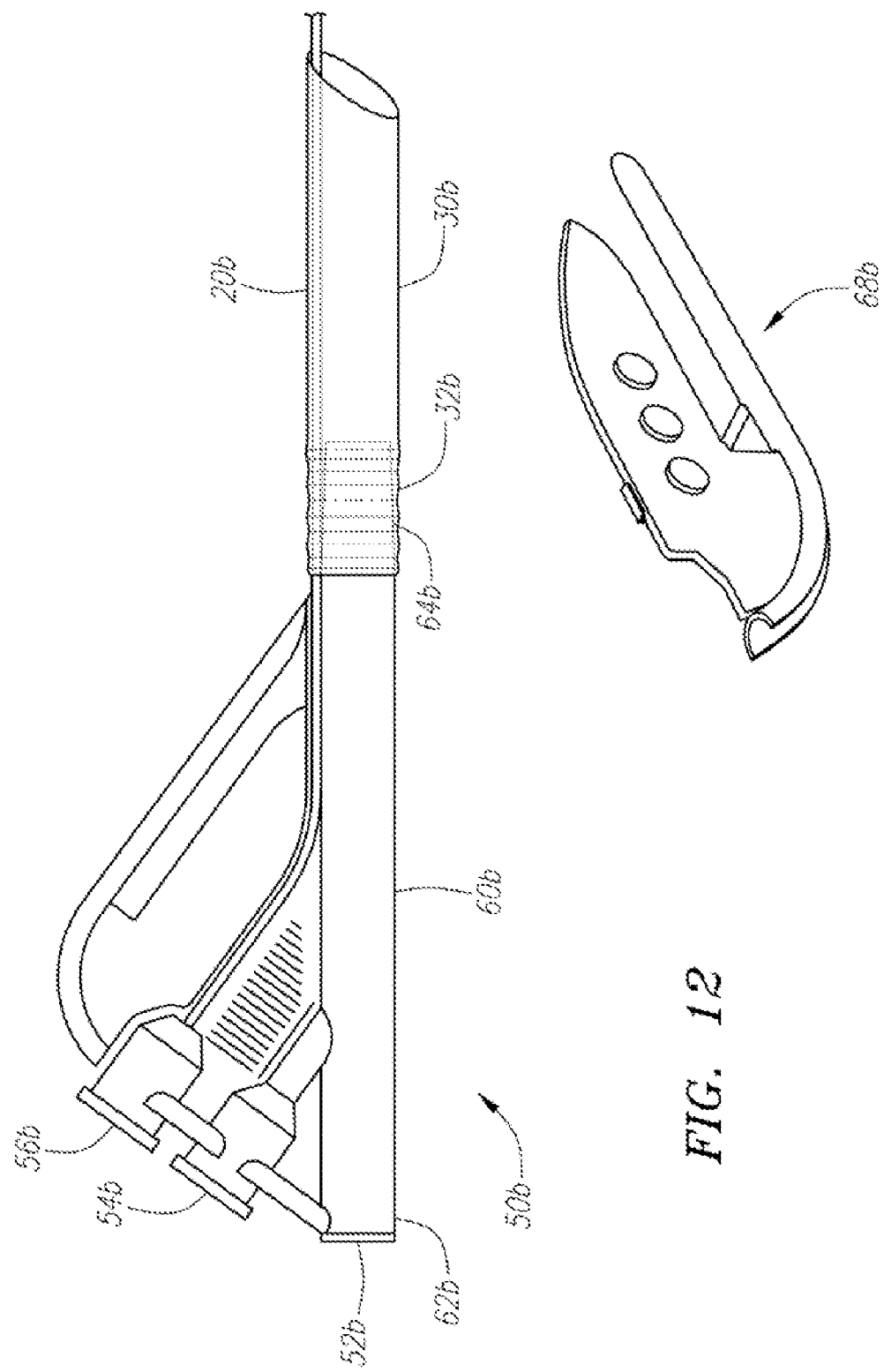
FIG. 12 is a side view of yet another embodiment of a handle apparatus, including a separate slitter.

Turning to FIG. 12, another embodiment of a handle 50b is shown that includes a separate slitter tool 68b, i.e., that is not attached to the handle 50b. Otherwise, the handle 50b may include a tubular section 60b, stiffening member 20, expandable sheath 30, and side ports 54b, 56b, similar to the previous embodiments.

Figure 13:
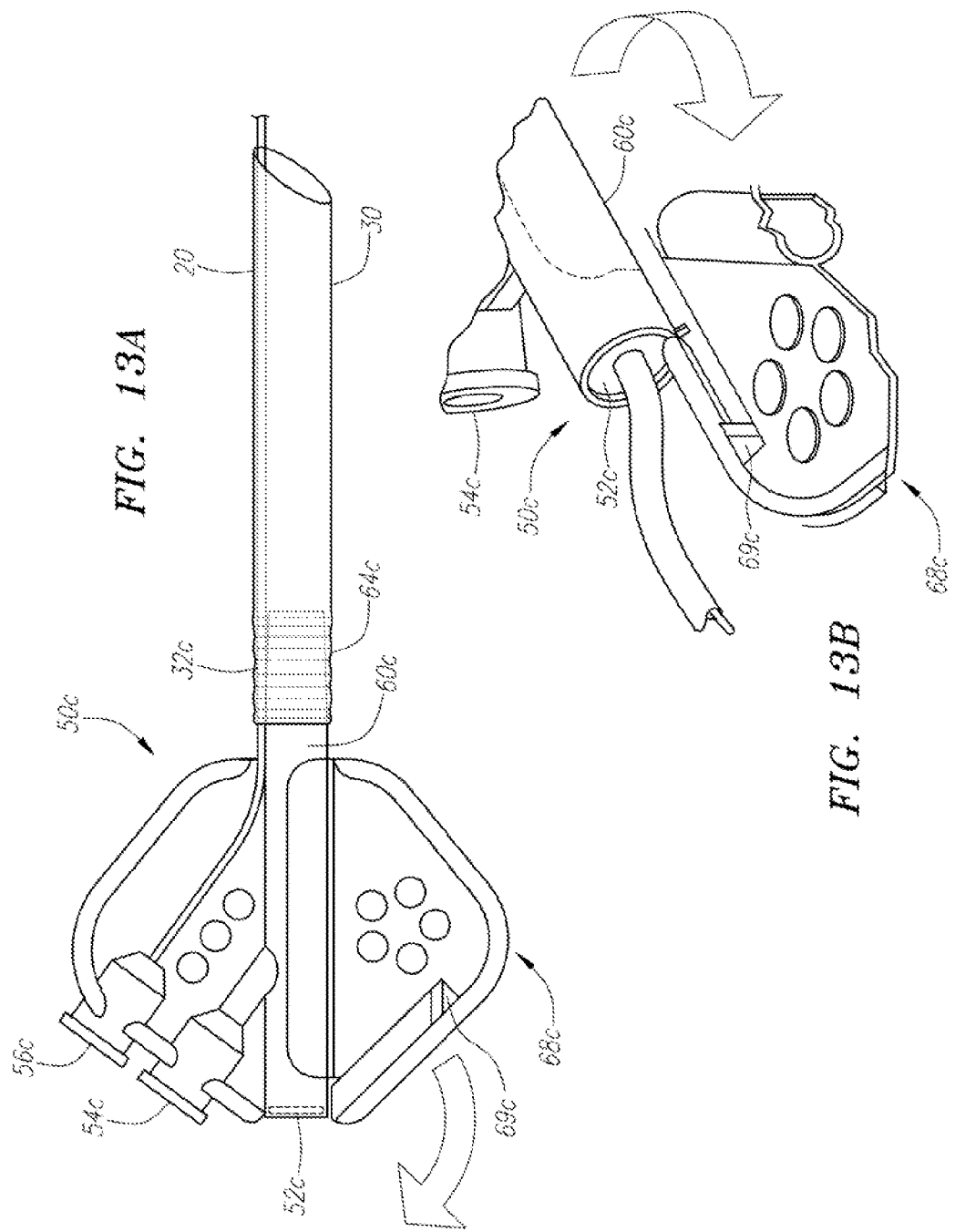
FIGS. 13A and 13B are side and perspective views, respectively, of still another embodiment of a handle apparatus including a pivotable slitter attached thereto.

Turning to FIGS. 13A and 13B, yet another embodiment of a handle 50c is shown that includes a tubular section 60c, stiffening member 20, expandable sheath 30, and side ports 54c, 56c, similar to the previous embodiments. A slitter tool 68c is attached to the tubular section 60c adjacent the seal 52c. The slitter tool 68c may be pivotally coupled to the tubular member 60c such that the slitter tool 68c may be pivoted to align a blade 69c of the slitter tool 68c with the tubular section 60c. Optionally, the tubular section 60c may include inner and outer portions (not shown), similar to the other embodiments described herein, such that the expandable sheath 30 may be split when the outer portion is withdrawn relative to the inner portion.

Figure 14:
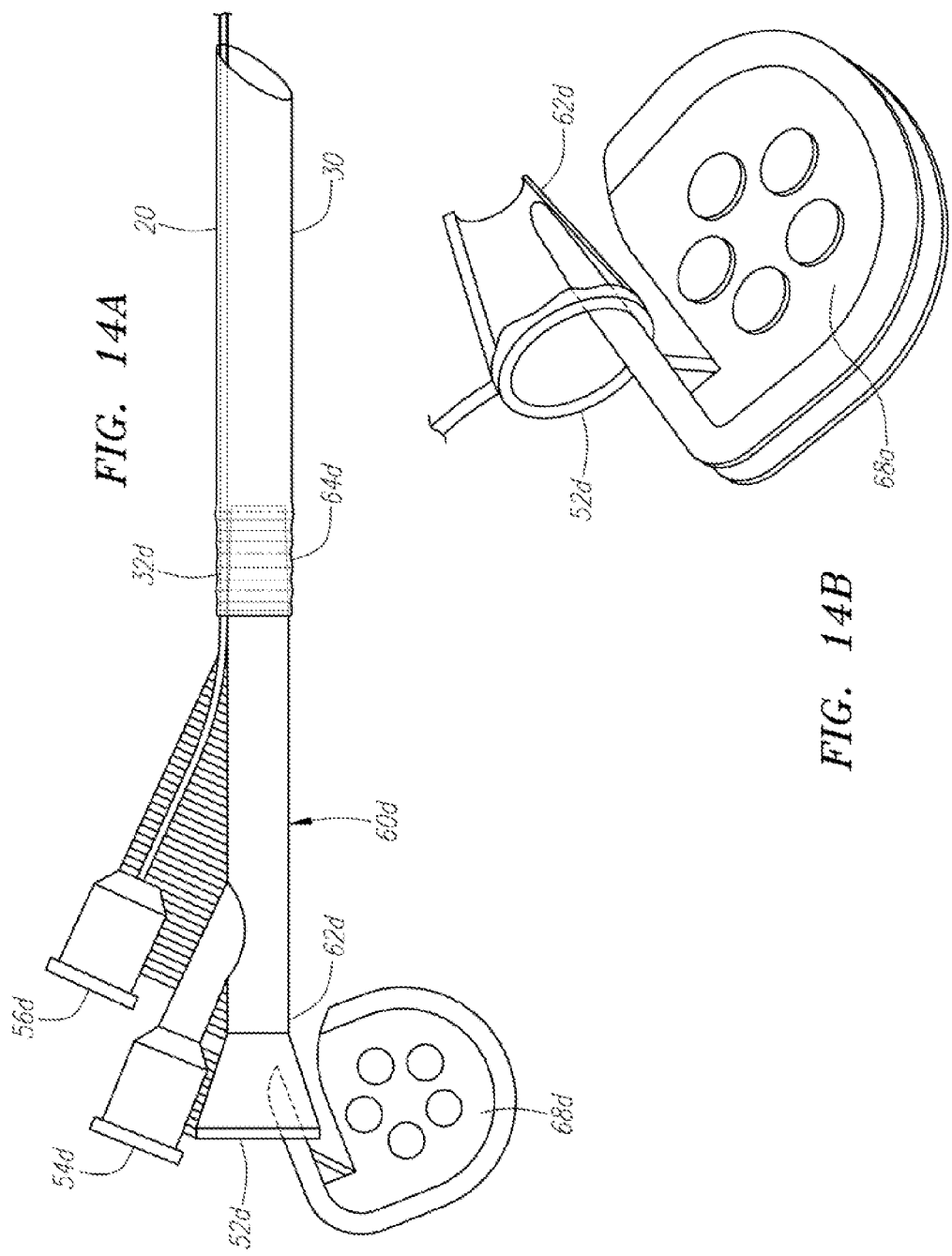
FIGS. 14A and 14B are side and perspective views, respectively, of another embodiment of a handle apparatus with an integral slitter.

Turning to FIGS. 14A and 14B, still another embodiment of a handle 50d is shown that includes a separate slitter tool 68d that may be manually inserted into a proximal end 60d of the tubular section 60d to split the tubular section 60d and the expandable sheath 30 attached thereto. The slitter tool 68d may be insertable into the seal 52d or may have a sharpened tip that may penetrate through the seal 52d to allow the tubular section 60d and sheath 30 to be split.

Figure 15:
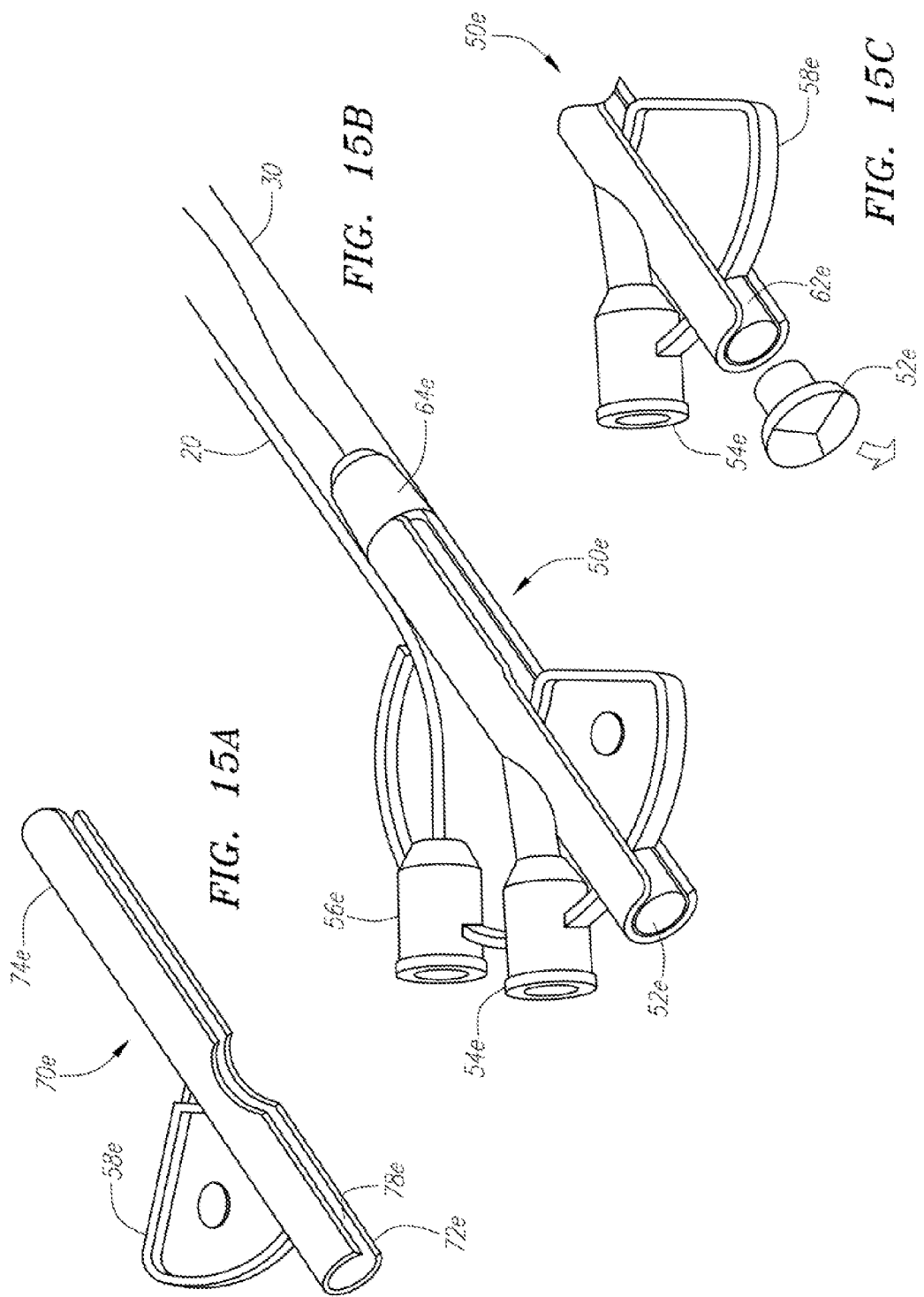
FIGS. 15A-15C are perspective views of yet another embodiment of a handle apparatus, including an outer member and an inner member slidable relative to one another.

FIGS. 15A-15C show another embodiment of a handle 50e that includes an inner member 60e and an outer member 70e. Similar to the previous embodiments, the inner member 60e may be slidably inserted into the outer member 70e such that a wing 58e of the inner member 60e is received in slot 78e in the outer member 70e. A stiffening member 20 and expandable sheath 30 may extend from the outer member 70e, similar to the previous embodiments. Unlike the previous embodiments, the hemostatic seal 52e may be removed from the inner member 60e.

Figure 16:
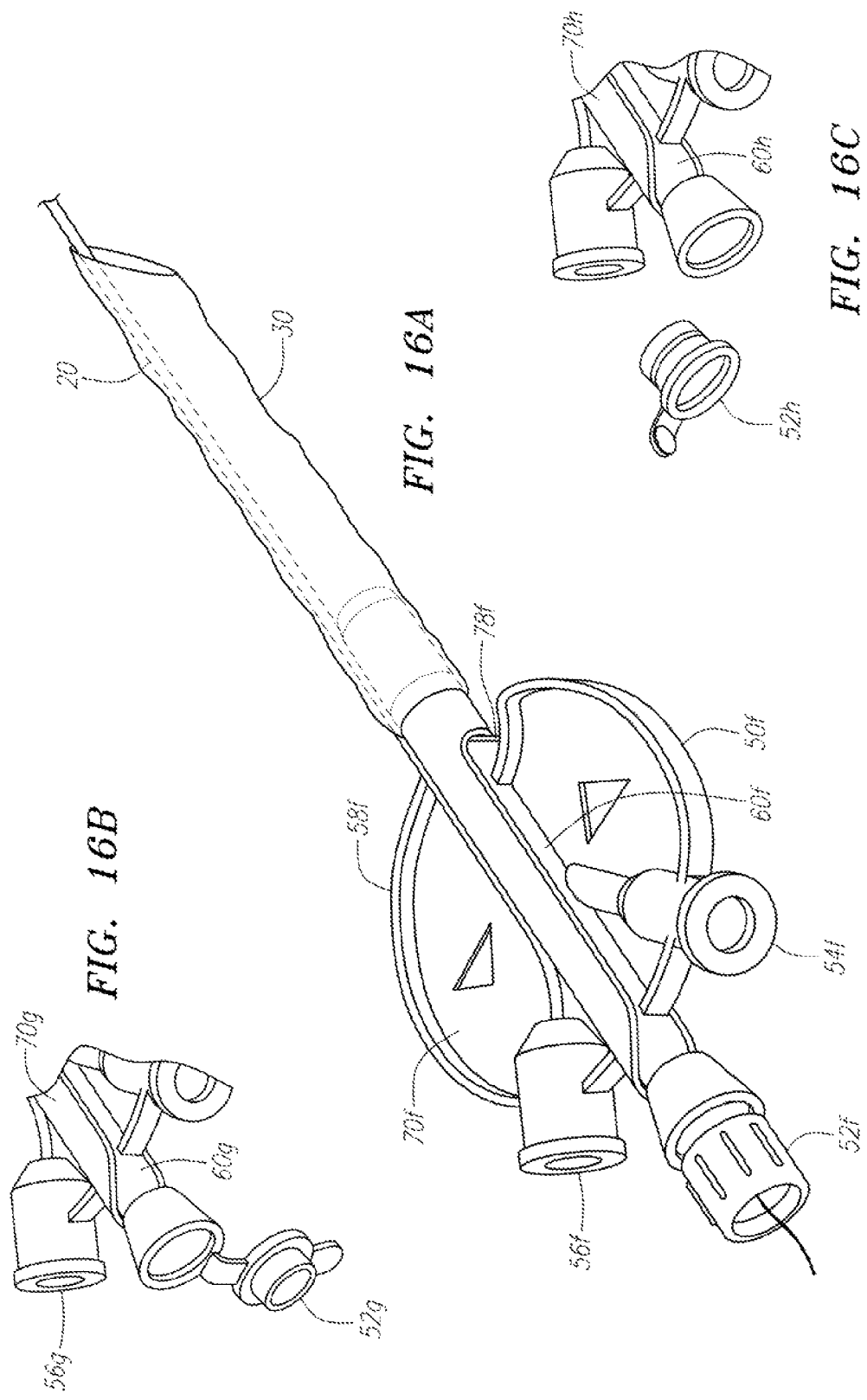
FIGS. 16A-16C are perspective views of alternative embodiments of a proximal end of a handle apparatus for a sheath apparatus.

FIGS. 16A-16C show alternative embodiments of a handle including a toughy borst valve 52f (FIG. 16A), a flip hemostatic valve 52g (FIG. 16B), and a completely removable hemostatic valve 52h (FIG. 16C). Such handles may allow the valve to be removed to facilitate using a slitter tool (not shown) to split the handle and/or sheath 30 extending therefrom.

During use, a sheath apparatus, such as apparatus 8 shown in FIG. 1A and described above (or other apparatus described herein), may be used to provide access to a vessel within a patient's body, e.g., a coronary vein. It will be appreciated that the sheath apparatus described herein may also be used to provide access to a variety of body lumens, e.g., to perform a diagnostic and/or therapeutic procedure, such as the those disclosed in application Ser. No. 10/423,321, incorporated by reference above.

Generally (with reference to FIG. 1A for illustration only), the apparatus 8, with the expandable sheath 30 in a contracted condition, may be introduced into an entry site, e.g., a natural or created opening in a patient's body, and advanced into one or more body passages, including natural or created passages within the patient's body. The apparatus 8 may be advanced from the entry site until a distal end 14 of the tubular proximal portion 10 is disposed at a first location, while the expandable distal portion 18 extends further to a second location. Because of its low profile, the expandable distal portion 18 may be easily advanced through tortuous anatomy until the distal tip 28 is disposed within relatively small, difficult to access body lumens. The tubular proximal portion 10 may provide enhanced support, e.g., to accommodate pushing one or more instruments (not shown) through the apparatus 8.

The sheath 30 may then be expanded to an enlarged condition, thereby defining a lumen 36 within the sheath 30. Thus, the apparatus 8 may provide a substantially continuous lumen, i.e., through the lumen 16 of the tubular proximal portion 10 and the lumen 36 of the sheath 30. The resulting lumen may extend continuously from the entry site through any intervening body passages to the target body lumen or site to provide a path from the entry site to the target body lumen or site.

A diagnostic and/or therapeutic procedure, such as the exemplary procedures described elsewhere herein, may be performed within the body lumen via the lumen defined by the apparatus 8. For example, one or more guidewires, catheters, leads, and the like may be advanced through the lumen provided by the apparatus 8. Upon completing the procedure (s), the apparatus 8 may be withdrawn from the body lumen, and entirely from the patient's body.

Figure 7:
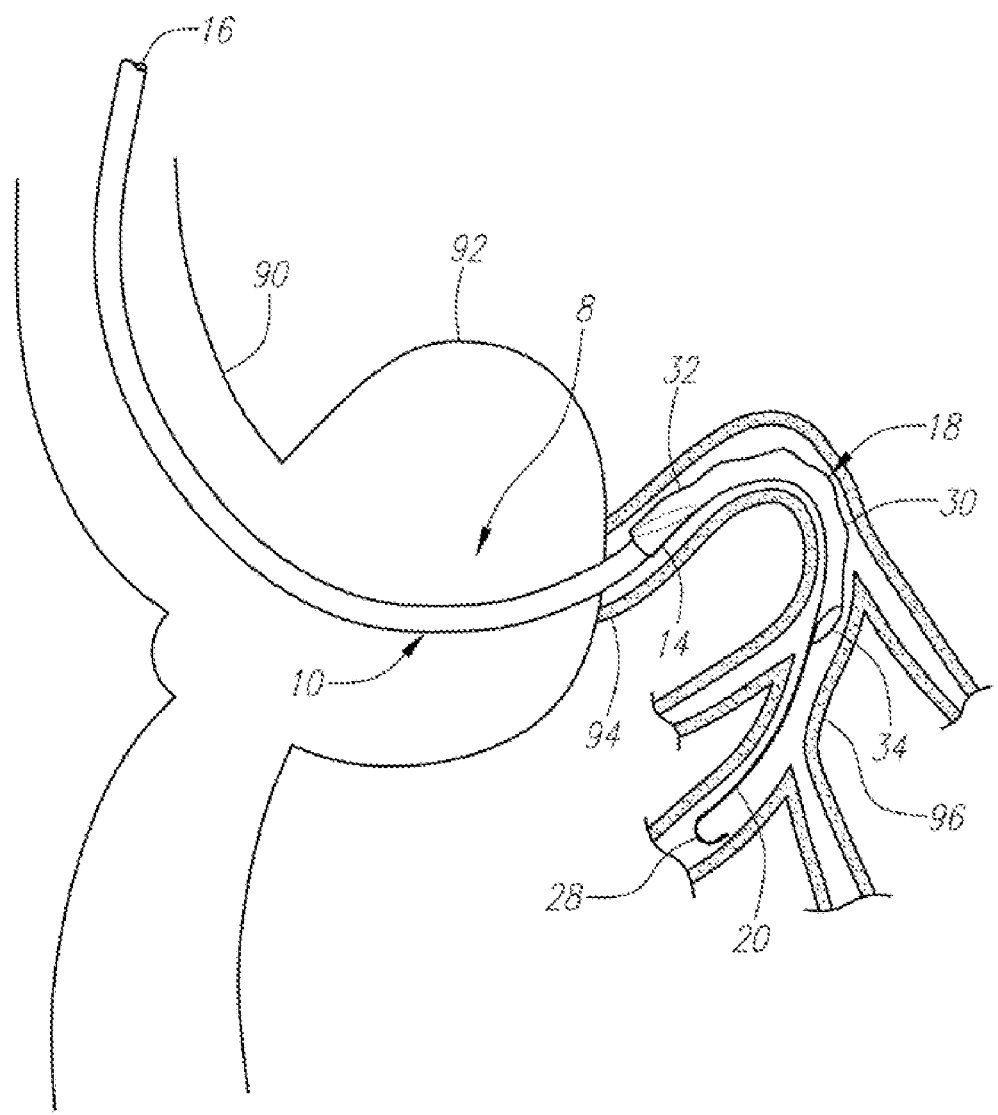
FIG. 7 is a cross-section of a patient's body, showing a method for accessing a vessel within the patient's heart using the apparatus of FIG. 1.

Turning to FIG. 7, an exemplary method is shown that uses a sheath apparatus 8 (or any of the sheath apparatus described herein) for providing access to a target vessel within a patient's vasculature. Specifically, the apparatus 8 may be used to deliver an electrical cardiac lead (not shown), e.g., for a pacemaker, into a coronary vein 96, e.g., adjacent to the left ventricle of the heart. Initially, the apparatus 8 may be advanced into the coronary vein 96 with an expandable sheath 30 carried by a stiffening member 20 in its contracted condition (not shown).

For example, with the sheath 30 collapsed, the apparatus 8 may be introduced from a percutaneous entry site, e.g., a femoral vein or subclavian vein (not shown), and advanced through the patient's venous system into the vena cava 90, the right atrium 92 of the heart, and finally into the coronary sinus 94 to reach the target coronary vein 96. The apparatus 8 may be advanced over a guidewire (not shown), e.g., by placing the guidewire along the desired path to the coronary vein 96 using conventional methods. Exemplary apparatus and methods for accessing the coronary sinus 94 to deliver the apparatus 8 are disclosed in co-pending application Ser. No. 10/447,526, filed May 29, 2003, the entire disclosure of which is expressly incorporated herein by reference.

Because of the relatively low profile of the expandable distal portion 18 with the sheath 30 collapsed (which is substantially the size of the stiffening member 20), the apparatus 8 may be able to access smaller coronary veins or be advanced further into a target coronary vein than the tubular proximal portion 10 or conventional access sheaths.

Thus, the distal portion 18 with the sheath 30 collapsed may be advanced first from the percutaneous site into the right atrium 92 and coronary sinus 94. As the apparatus 8 is advanced further, the distal tip 28 of the distal portion 18 may be introduced into the target vein 96. As this occurs, the proximal portion 10 may pass through the vena cava 90 and into the right atrium 92, or even the coronary sinus 94, as shown. Because the proximal portion 10 may only pass through larger, less tortuous vessels, the larger profile may not impair advancement of the apparatus 8 to place the distal tip within the target vein 96.

If the distal portion 10 has a tapered distal end 14, the distal end 14 may also provide a transition to facilitate the tubular portion 10 following the smaller distal portion 18. In addition or alternatively, as shown in FIG. 20, an obturator 40 may be provided within the apparatus 8 to facilitate advancing the proximal portion 10 after the distal portion 18. Once the proximal portion 10 is adequately positioned, e.g., within the right atrium 92 or coronary sinus 94, the obturator 40 may be removed.

Once the apparatus 8 is positioned with the expandable distal portion 18 in or near the target vein 96, fluoroscopy and/or other external imaging may be used to facilitate positioning the apparatus 8. Optionally, the apparatus 8 may include one or more radiopaque markers, e.g., on the distal end 24 of the stiffening member 20, the distal end 34 of the sheath 30, and/or the distal end 14 of the proximal tubular portion 10, to facilitate such imaging. In addition or alternatively, contrast may be introduced into the vein, e.g., via a fluid lumen in the stiffening member 20 of the apparatus 8 and/or through the lumen 34 of the sheath 30, to facilitate fluoroscopic imaging. Such imaging may be used to identify the location of the sheath 30 relative to nearby structures, e.g., to ensure that the apparatus 8 is advanced as close as possible to a target location. In the exemplary embodiment shown in FIG. 7, the apparatus 8 is advanced such that the distal end 34 of the sheath 30 is disposed within a coronary vein 96 adjacent the left ventricle of the patient's heart.

The expandable sheath 30 may then be expanded between the distal end 14 of the proximal tubular portion 10 and the target vein 96. A fluid, e.g., including saline and/or contrast, may be introduced into the sheath 30 to expand the sheath 30 towards its enlarged condition. Contrast delivered into the sheath 30 may also facilitate imaging the vein 96. In addition or alternatively, an instrument (not shown) may be advanced through the apparatus 8 to expand the sheath 30.

An electrical pacing lead (not shown) and/or other instrument may then be advanced through the proximal tubular portion 10 and the sheath 30 (which may expand or further expand the sheath 30) until the lead is disposed within the vein 96 beyond the distal tip 28. Because cardiac leads are extremely flexible or floppy, the relative strength and/or rigidity of the proximal portion 10 may facilitate advancing the lead through larger vessels, where the lead may otherwise wander or bind up. As the lead enters the sheath 30, the sheath 30 may provide a lubricious interface between the lead and the surrounding vessel wall, which may facilitate advancing the lead deeper into the patient's vasculature.

Once the lead is delivered, the apparatus 8 may be removed. For example, as described above, a handle, such as handle 50 described above (not shown in FIG. 7, see FIGS. 9-10C), may be provided that includes an inner member 60 and an outer member 70 to which the tubular proximal portion 10 is attached. In this embodiment, the cardiac lead may be advanced into the inner member 60 through the valve 52, and, consequently into the proximal portion 10 and sheath 30.

To remove the apparatus 8, the outer member 70 may be retracted proximally, thereby withdrawing the tubular proximal portion 10, as well as the distal portion 18 (i.e., the stiffening member 20 and sheath 30), proximally from the patient's body. As the sheath 30 is removed from the percutaneous site, the sheath 30 may be split, e.g., by a blade 78 or other slitter tool (not shown) on the inner member 60.

While the outer member 70, tubular proximal portion 10 and expandable distal portion 18 are removed, the inner member 60 may be maintained substantially stationary, thereby maintaining the end of the lead within the target vein 96. Once the tubular proximal portion 10 and sheath 30 are removed from the patient, the inner member 60 may also be removed, while maintaining the lead substantially stationary. Because the inner member 60 has a relatively short length, the inner member 60 may be removed more easily with reduced risk of displacement of the lead, thereby ensuring that the lead remains within the target vein 96.

Figure 8A:
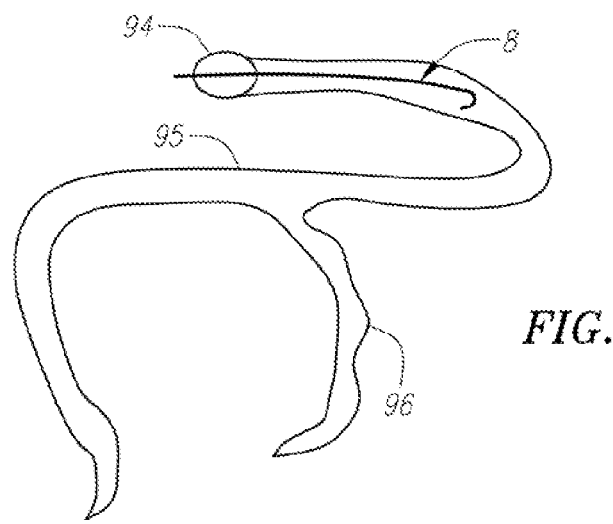
FIGS. 8A-8J are cross-sections of a patient's body, showing a method for delivering a cardiac lead into a coronary vein within a patient's heart.
Figure 8B:
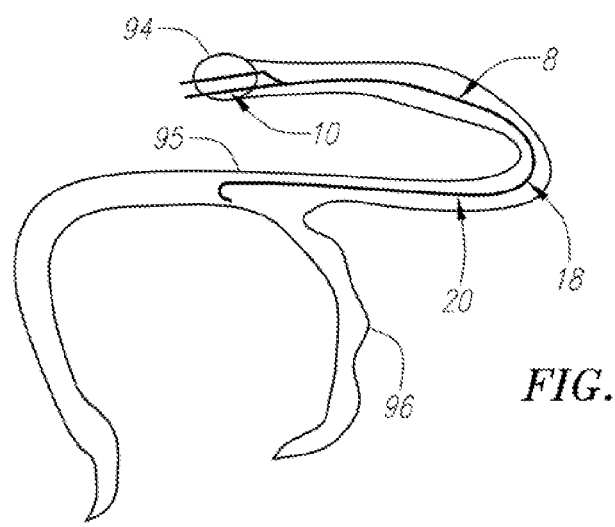
Figure 8C:
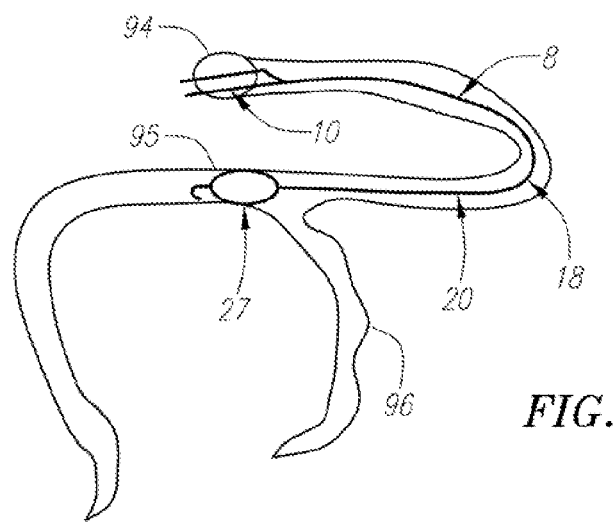

Turning to FIGS. 8A-8J, another method is shown for delivering an electrical pacing lead 100 into a coronary vein 96, e.g., through the right atrium (not shown) and coronary sinus 94 of the heart, similar to the previous embodiment. This method may be particularly useful for delivering a lead into a target vein 96 that is difficult to access, e.g., if it branches acutely from an adjacent vessel 95. Initially, as shown in FIGS. 8A-8C, an apparatus 8 may be introduced through the coronary sinus 94 into the vessel 95 adjacent the target vein 96. Generally, the apparatus 8 includes a tubular proximal portion 10, and an expandable distal portion 18, similar to the previous embodiments. The distal portion 18 includes a pushable stiffening member 20 carrying a balloon 27 or other expandable occlusion member and an expandable sheath 30.

As shown in FIGS. 8A and 8B, the apparatus 8 may be advanced into the vessel 95 with the sheath 30 and balloon 27 initially collapsed. The apparatus 8 may be advanced over a guidewire or other rail (not shown). Optionally, contrast and the like may delivered via a lumen in the stiffening member 20 to facilitate fluoroscopic imaging of the patient's vasculature, e.g., to facilitate advancing the apparatus 8, and/or positioning the balloon 27 distally to the target vein 96. Alternatively, the balloon 27 may be provided on a separate catheter or other balloon device (not shown), and the apparatus 8 may be advanced over the balloon device.

As shown in FIG. 8C, once the balloon 27 is positioned at a desired location, e.g., immediately distal to the target vein 96, the balloon 104 may be expanded to at least partially occlude the vessel 95 and/or to substantially seal the vessel 95 distal to the target vein 96 (e.g., if additional contrast delivery is desired for fluoroscopic imaging). In addition, the balloon 27 may substantially anchor the stiffening member 20 relative to the target vein. As shown in FIG. 8C, the tubular proximal portion 10 may be sufficiently long to enter the coronary sinus 94 when the balloon 27 is positioned adjacent the target vein 96.

Figure 8D:
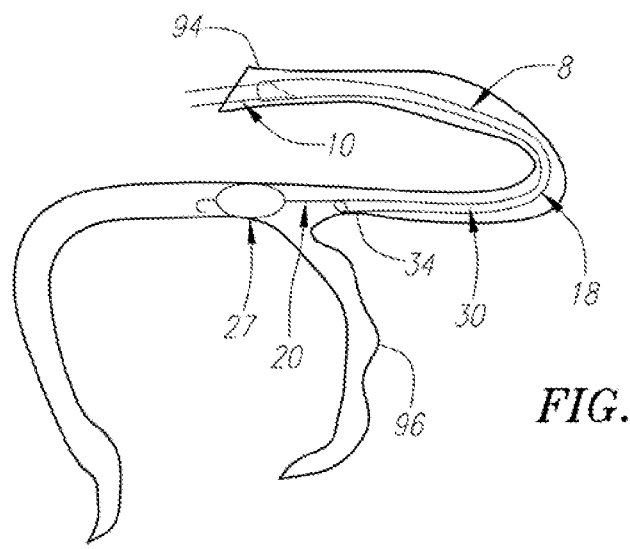

Turning to FIG. 8D, once the balloon 27 is positioned and expanded to occlude the vessel 95 and/or anchor the stiffening member 20, the sheath 30 may be expanded, if desired. Alternatively, the sheath 30 may remain collapsed (but may be released from any constraints) until the lead 100 is advanced into the sheath 30. In a further, alternative, the sheath 30 may be expanded before the balloon 27 is expanded.

Figure 8E:
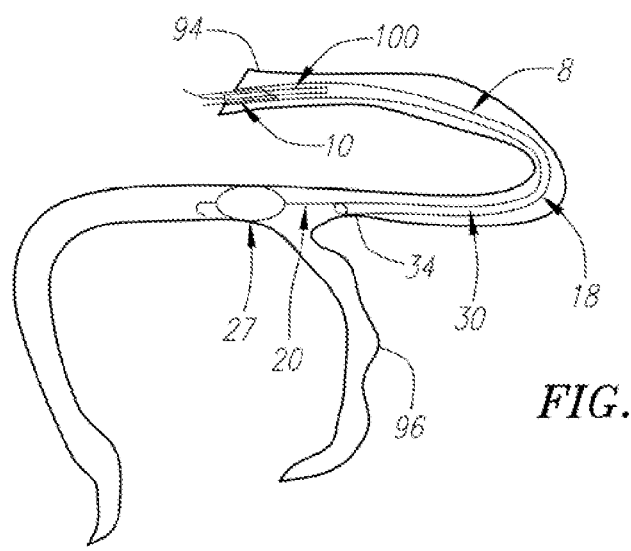
Figure 8F:
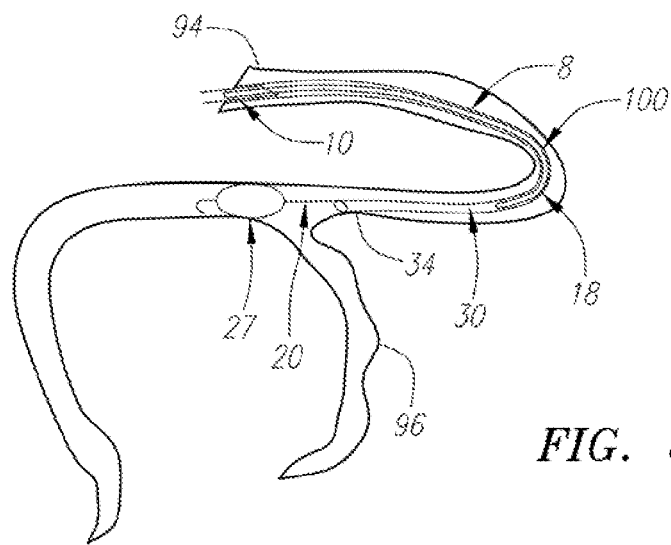

Turning to FIGS. 8E-8H, a lead 100 may then be advanced through the apparatus 8 into the target vein 96. For example, the lead 100 may be inserted through a valve 52 of a handle 50 on a proximal end 12 (all not shown, see, e.g., FIG. 1A) of the apparatus 8 into the tubular proximal portion 10 and advanced until the lead 100 enters the expandable distal portion 18, as shown in FIG. 8E. As the lead 100 is advanced further, the sheath 30 may expand or otherwise accommodate guiding the lead 100 through the coronary veins into vessel 95, as shown in FIGS. 8E and 8F.

Figure 8G:
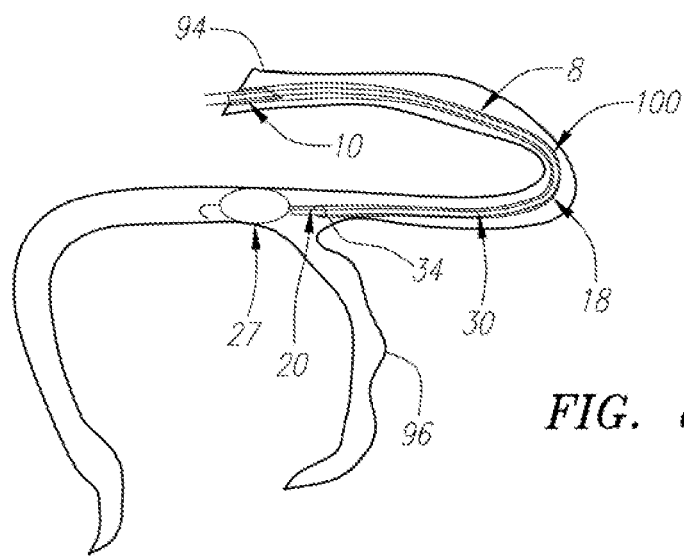
Figure 8H:
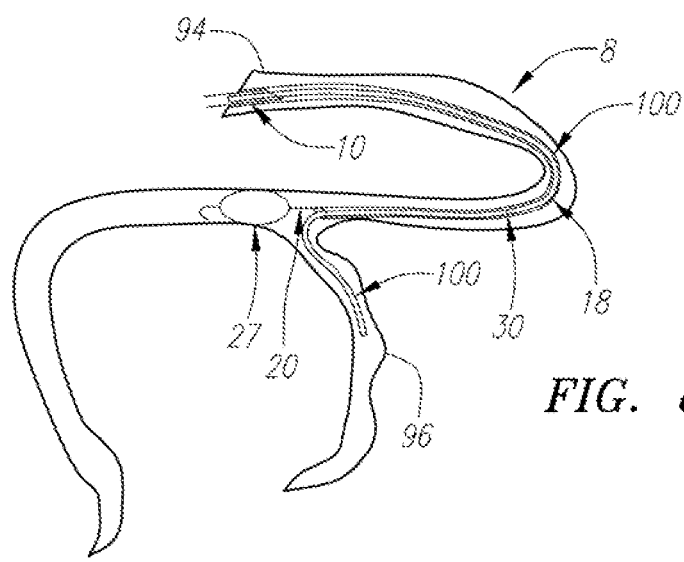

Turning to FIG. 8G, the lead 100 may eventually exit from the distal end 34 of the sheath 30 and become exposed within the vessel 95. As the lead 100 is advanced further, the lead 100 may contact the balloon 27. Because the balloon 27 substantially occludes the vessel 95 distal to the target vein 96, as the lead 100 is advanced further, the only available path is into the target vein 96. Thus, the balloon 27 may assist in redirecting the lead 100 into a target vein 96 that may otherwise be difficult to access, as shown in FIG. 8H.

Figure 8I:
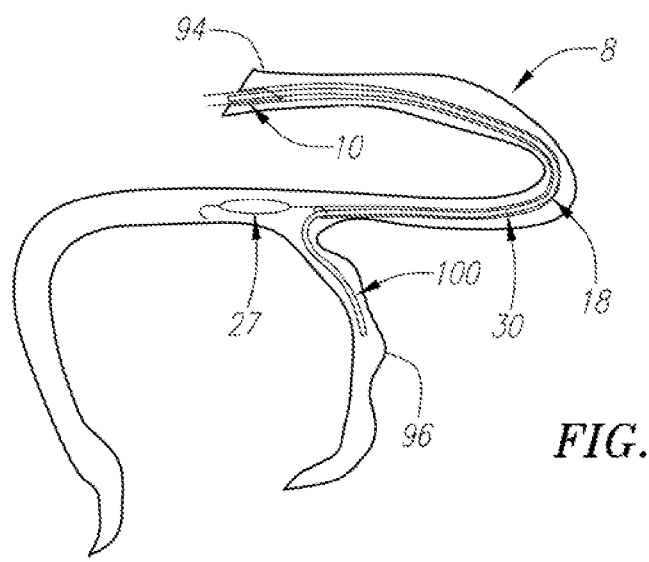
Figure 8J:
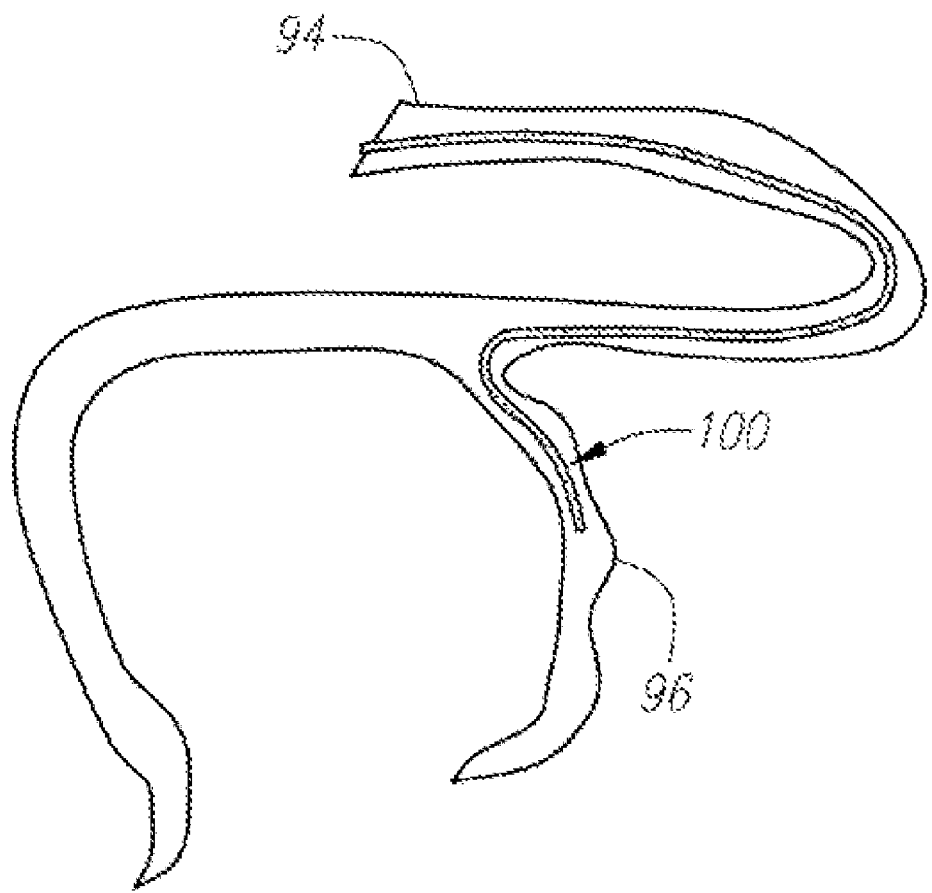

Turning to FIG. 8I, once the lead 100 is positioned in the target vein 96, the balloon 27 may be deflated or otherwise collapsed, and the apparatus 8 may be withdrawn from the vessel 95, the coronary sinus 94, and ultimately out of the patient's body. As shown in FIG. 8J, the lead 100 may remain implanted within the target vein 96 (or further down another branch, if desired). Implantation of the lead 70 may then be completed, e.g., including connecting the proximal end to a pacemaker and the like (not shown), using conventional methods.

Figure 19A:
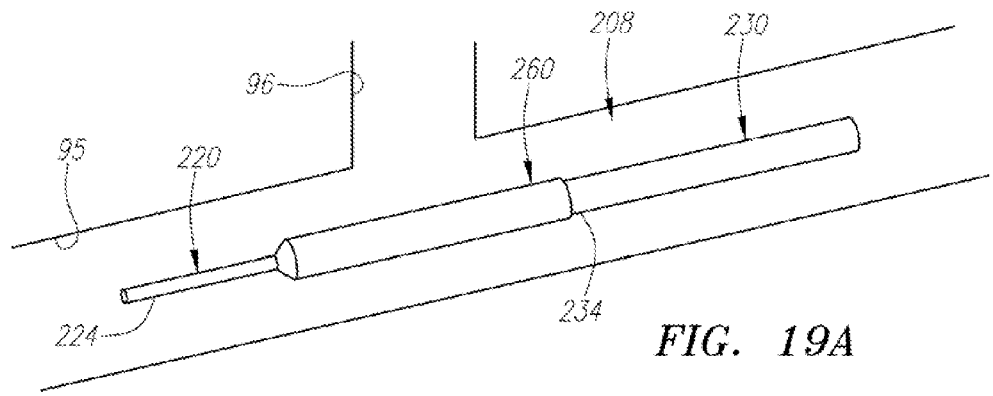
FIGS. 19A-19C are cross-sectional views of a patient's body, showing a method for delivering a lead into a branch vessel from a main vessel.
Figure 19B:
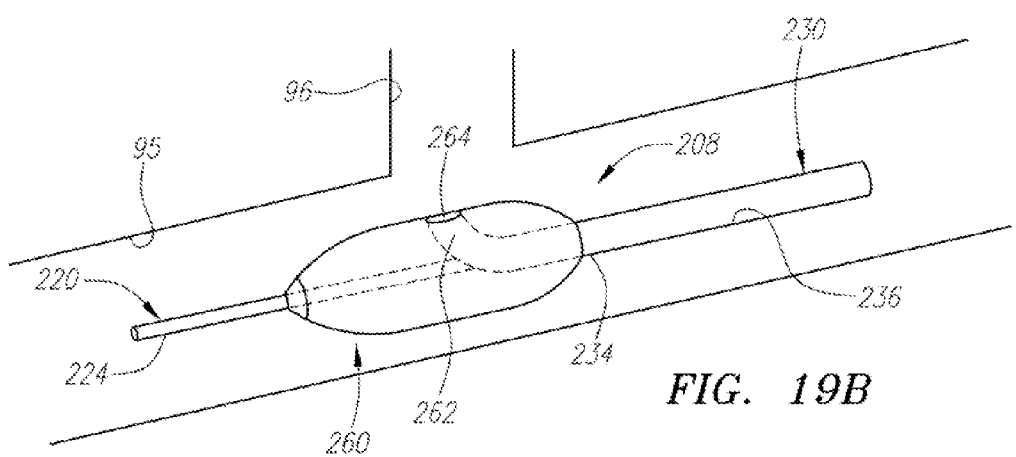
Figure 19C:
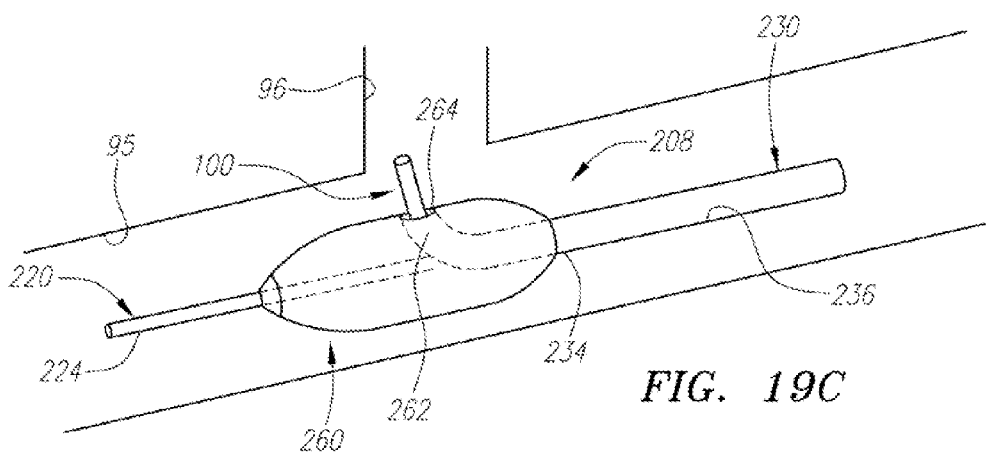

Turning to FIGS. 19A-19C, in an alternative embodiment, an expandable sheath apparatus 208 may be provided that includes a stiffening member 220 and an expandable sheath 230, similar to the other embodiments described herein. Optionally, the apparatus 208 may include one or more of a tubular proximal portion, a handle, and the like (all not shown), also similar to the embodiments described above.

Unlike the previous embodiments, the apparatus 208 includes a balloon or other expandable member 260 on a distal end 234 of the sheath 230. The stiffening member 220 or sheath 230 may include a lumen (not shown) that communicates with an interior of the balloon 260, for delivering inflation media into the balloon 260 from a proximal end (not shown) of the apparatus 208. Thus, the balloon 260 may be expanded or collapsed by delivering or evacuating fluid into and out of the balloon 260.

As best seen in FIG. 19B, the balloon 260 includes a passage 262 therethrough that communicates with a lumen 236 of the sheath 230. As shown, the passage 260 includes a bend that terminates in a transverse opening 264 in an outer wall of the balloon 260. As shown, the passage 260 extends substantially perpendicular to the stiffening member 220, although it will be appreciated that the passage 260 and opening 264 may provide any desired lateral or other transverse orientation.

The apparatus 208 may be used for delivering a lead 100, similar to the previous embodiments. For example, as shown in FIG. 19A, with the sheath 230 and balloon 260 collapsed, the apparatus 8 may be advanced into a vessel 95 until the balloon 260 is disposed adjacent to a target vessel 96. Once properly positioned, the balloon 260 may be expanded, e.g., to open the passage 262 and/or to anchor the apparatus 208 relative to the vessel 95. As best seen in FIG. 19B, the balloon 208 is preferably expanded with the opening 264 disposed in alignment with the target vessel 96.

Thereafter, as shown in FIG. 19C, a lead 100 may be advanced through the apparatus 208, i.e., through the lumen 236 of the sheath 230 until the lead 236 enters the passage 262. Because of the floppy structure of the lead 100 and/or the radius of the passage 262, the lead 100 may be advanced through the passage 262, out the opening 264, and into the target vessel 96. The lead 100 may then be implanted within the target vessel 96 or otherwise further manipulated, as desired. Once the lead 100 is positioned at a desired implantation site, the balloon 260 may be collapsed, and the apparatus 208 may be removed from the vessel 95 and out of the patient's body.

Figure 17:
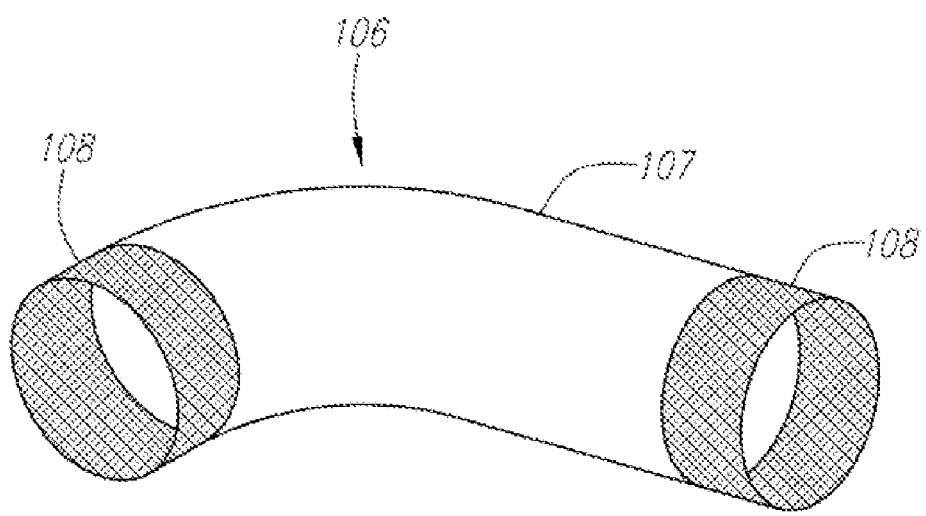
FIG. 17 is a perspective view of a protective sleeve that may be carried by a cardiac lead.

Turning to FIGS. 17 and 18A-18C, a thin sleeve 106 is shown that may be delivered in conjunction with a lead 100, e.g., a cardiac pacing lead. As best seen in FIG. 17, the sleeve 106 may include a tubular section 107 and a stent-like structure 108 on one or both ends of the tubular section 107. It will be appreciated that any self-expanding or balloon-expandable stent structures may be provided on the ends of the tubular section 107.

Figure 18A:
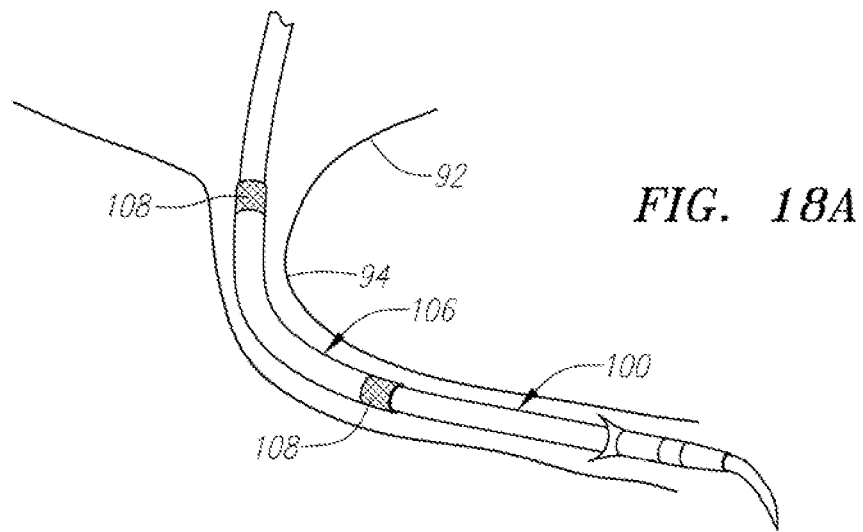
FIGS. 18A-18C are cross-sectional views of a patient's body, showing a method for delivering and removing a removable cardiac lead into the patient's heart that includes the protective sleeve of FIG. 17.

Turning to FIG. 18A, in one embodiment, the thin sleeve 106 may be provided on an exterior of a lead 100, e.g., at an intermediate location on the lead 100. Otherwise, the lead 100 may be of conventional, known construction. The lead 100, carrying the sleeve 106, may be delivered into a patient's body, e.g., through the right atrium 92, the coronary sinus 94, and into the coronary veins (not shown). Preferably, the sleeve 106 is provided at a predetermined intermediate location on the lead 110, such that, when a tip of the lead is delivered into a target vein, the sleeve 106 is disposed within the coronary sinus 96, as shown in FIG. 18A. The lead 100 may be delivered using the apparatus and methods described herein, or using conventional methods.

Generally, after a lead, such as lead 100, is implanted, the wall of the coronary sinus may fibrose or otherwise attach to the lead 100. Because the sleeve 106 is disposed around the lead 100, any tissue fibrosis may attach to the sleeve 106, rather than to the lead 100 itself. Thereafter, if it is desired to remove or move the lead 100 (e.g., as often becomes necessary over time as the heart remodels itself to CRT therapy), the lead 100 may be manipulated or even removed, while the sleeve 106 remains in place. Without the sleeve 106, if the lead 100 is removed or otherwise moved, there is a substantial risk that the wall of the coronary sinus may rupture or otherwise be damaged due to the tissue fibrosis, requiring acute treatment of the patient.

Figure 18B:
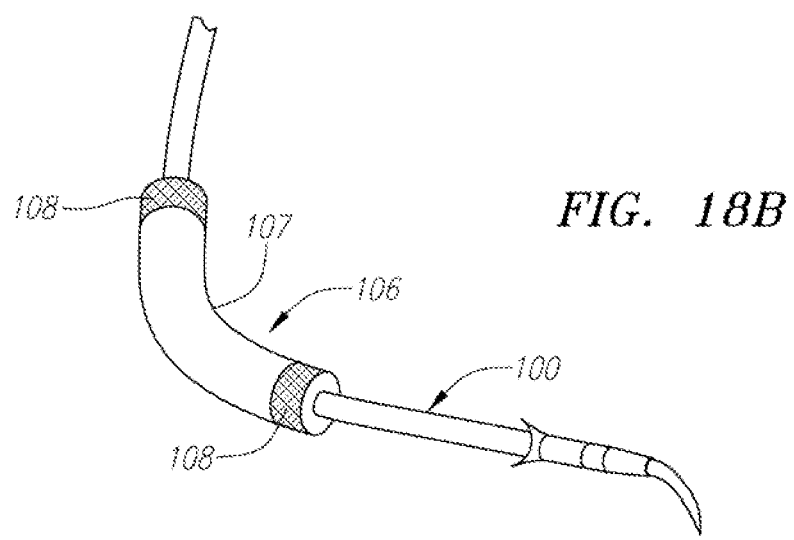
Figure 18C:
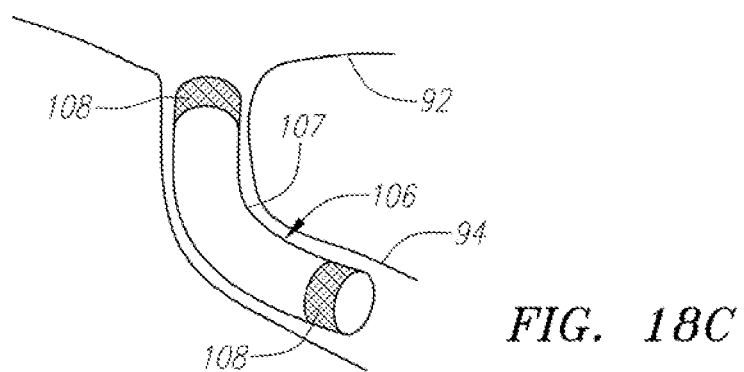

Optionally, as shown in FIG. 18B, a balloon device may be used to expand the thin sleeve 106, e.g., to plastically expand the stents 108 into engagement with the surrounding tissue of the coronary sinus 96. Alternatively, an overlying sleeve or other constraint may be used to hold the thin sleeve 106, such that, when the constraint is removed, the thin sleeve 106 may resiliently expand to engage the tissue of the coronary sinus 96.

Such a balloon or constraint may be provided on the lead 100 or on an apparatus (not shown) used to deliver the lead 100, e.g., on an exterior of a proximal portion of any of the apparatus described herein. Alternatively, the thin sleeve 106 may be delivered independently, e.g., before the lead 100 is delivered through the coronary sinus 96.

In other alternatives, the lead may include a drug or other material embedded within or otherwise carried by the lead that may prevent or minimize tissue fibrosis to the lead. In addition or alternatively, the outer surface of the lead may be treated, e.g., by micro-texturing that may prevent surrounding tissue from binding to the lead.

Turning to FIGS. 24A and 24B, another embodiment of an expandable sheath apparatus 109 is shown that includes an elongate stiffening member 120 having a proximal end 122 and a distal end 124. The apparatus 109 further includes a flexible sheath 130 affixed or otherwise secured to the elongate stiffening member 130 along its length. The flexible sheath 130 is shown in a collapsed state in FIG. 24A, and is shown in an expanded or partially expanded state in FIG. 24B.

The flexible sheath 130 may be affixed or otherwise secured to the elongate stiffening member 120 using any number of configurations. FIGS. 25-31 are cross-sectional views of alternative embodiments of the apparatus 109, taken along the line A-A shown in FIG. 24A.

FIG. 25 illustrates a cross-sectional view of the distal portion of the apparatus 109 illustrating one embodiment of securing the elongate stiffening member 120 to the sheath 130. In this embodiment, the elongate stiffening member 120 is external to the lumen of the sheath 130. The elongate stiffening member 120 is slit along its length to form a slot 120(a). A portion of the flexible sheath 30 is then inserted into the slot 120(a) and into the interior lumen 120(b) of the elongate stiffening member 120. The portion of the flexible sheath 130 inside the elongate stiffening member 120 may then be affixed or otherwise bonded to the internal surface 120(c) of the elongate stiffening member 120.

In an alternative embodiment, a secondary tube 121 may be inserted through the lumen 120(b) of the elongate stiffening member 120 such that the sheath 130 is sandwiched between the exterior of the secondary tube 121 and the internal surface 120(c) of the elongate stiffening member 120. A mechanical junction is formed between elongate stiffening member 120 and the flexible sheath 130. This structure is particularly advantageous for materials that are difficult to heat or chemically bond, such as fluoropolymers. For example, the elongate stiffening member 120 and secondary tube 121 may be constructed out of a polymer material that reflows with heat (e.g., ePTFE) or a material coated with flowable polymer material. A mechanical lock may be achieved between the elongate stiffening member 120 and secondary tube 121 upon the reflowing of polymer material through the pores of the ePTFE within the sheath 130.

FIG. 26 is a cross-sectional view of the distal portion of the apparatus 109, illustrating another construction for securing the elongate stiffening member 120 to the sheath 130. In this embodiment, the sheath 130 is formed into first and second separate lumens 130' and 130." The first lumen 130' is the primary lumen through which an instrument, such as an electrical pacing lead, passes. The elongate stiffening member 120 is received in the second lumen 130." The elongate stiffening member 120 may be bonded along its entire length or at intervals to an interior surface 130(a) of the second lumen 130." Alternatively, as is shown in FIG. 26, the elongate stiffening member 120 may be slidable within the second lumen 130." In the embodiment shown in FIG. 26, the sheath 130 having first and second lumens 130,' 130" is preferably formed by co-extruding a polymer material of the type described above.

FIG. 27 illustrates a cross-sectional view of the distal portion of the apparatus 109, illustrating still another construction for securing the elongate stiffening member 120 to the sheath 130. Similar to the embodiment discussed above and shown in FIG. 27, the sheath 130 is formed into first and second separate lumens 130' and 130." The first lumen 130' is the primary lumen through which an instrument, such as an electrical pacing lead, passes. The second lumen 130" contains the elongate stiffening member 120. The elongate stiffening member 120 may be bonded along its entire length or at intervals to an interior surface 130(a) of the second lumen 130." Alternatively, as is shown in FIG. 27, the elongate stiffening member 120 may be slidable within the second lumen 130." The first and second lumens 130', 130" of the sheath 130 are joined by a spine 130(b), which preferably runs along the entire length of the sheath 130. The first and second lumens 130', 130" are preferably formed by co-extruding a polymer material of the type described above. In an alternative configuration, the spine 130(b) may be formed from a bonding material that links or otherwise connects the first and second lumens 130', 130" of the flexible sheath 130.

Figure 28:
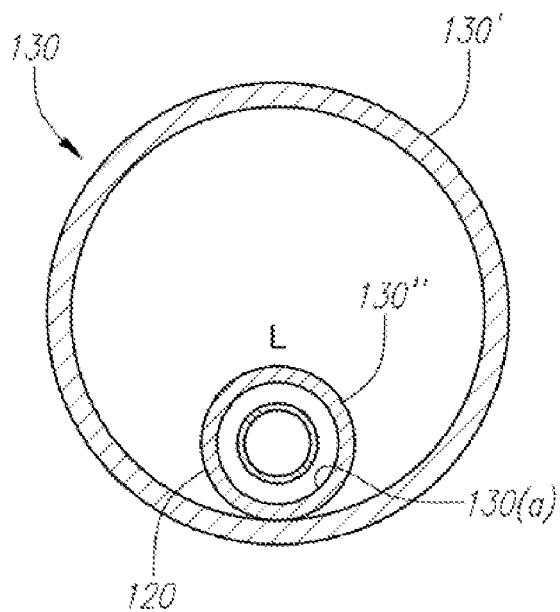

FIG. 28 shows a cross-sectional view of the distal portion of the apparatus 109, illustrating still another construction for securing the elongate stiffening member 120 to the sheath 130. In this embodiment, the second lumen 130" is located within the primary lumen 130' of the flexible sheath 130. The elongate stiffening member 120 is disposed within the second lumen 130" and may be bonded to an interior surface, or, alternatively, may be slidable therein. The advantage to the embodiment shown in FIG. 28 is that the profile of the apparatus 109 may be reduced, thereby making it easier to advance the apparatus 109 within particularly narrow passageways or vessels.

Figure 29:
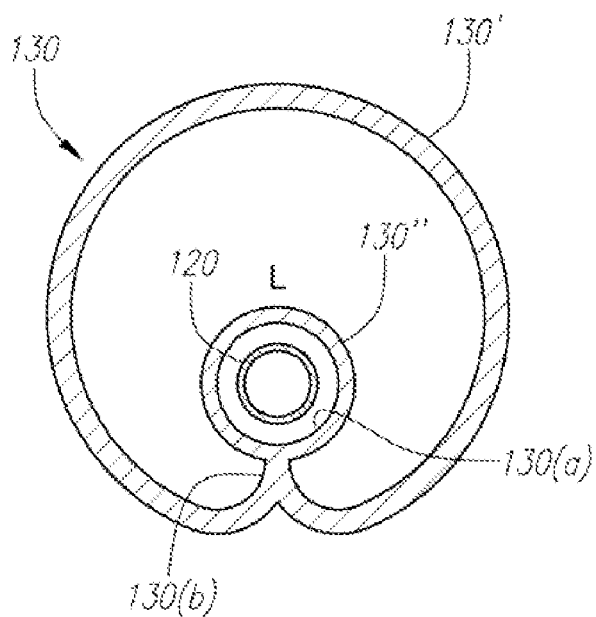

FIG. 29 illustrates yet another configuration of the distal end of the apparatus 109. In this embodiment, the structure shown in FIG. 27 may be inverted, thereby placing the second lumen 130" within the interior of the primary lumen 130' of the sheath 130. The inverting process may be accomplished by pulling an end of the sheath 130 shown in FIG. 27 through the primary lumen 130.' This embodiment is particularly advantageous for two reasons. First, the cross-sectional profile may be reduced by placing the second lumen 130" within the interior of the primary lumen 130.' Second, the spine 130(b) may serve as a barrier that prevents an instrument, such as an electrical pacing lead, from coiling or wrapping around the second lumen 130."

Figure 30A:
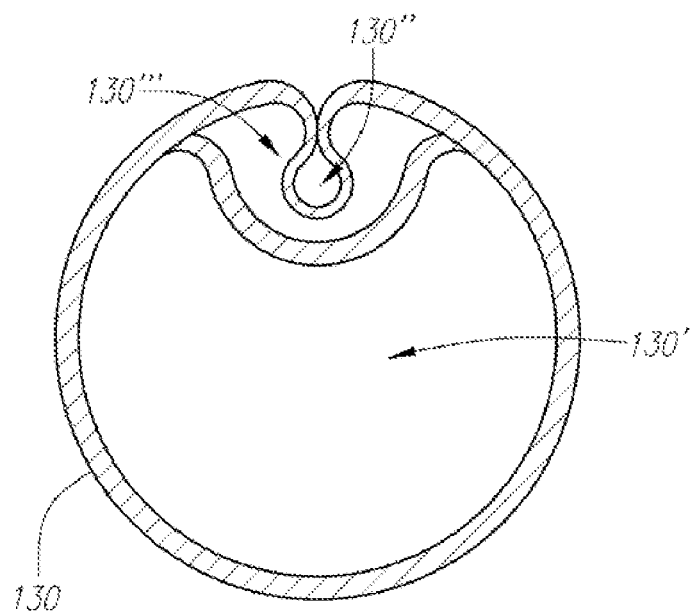
FIGS. 30A and 30B are cross-sectional views of additional alternative configurations of the sheath apparatus of FIGS. 24A and 24B.
Figure 30B:
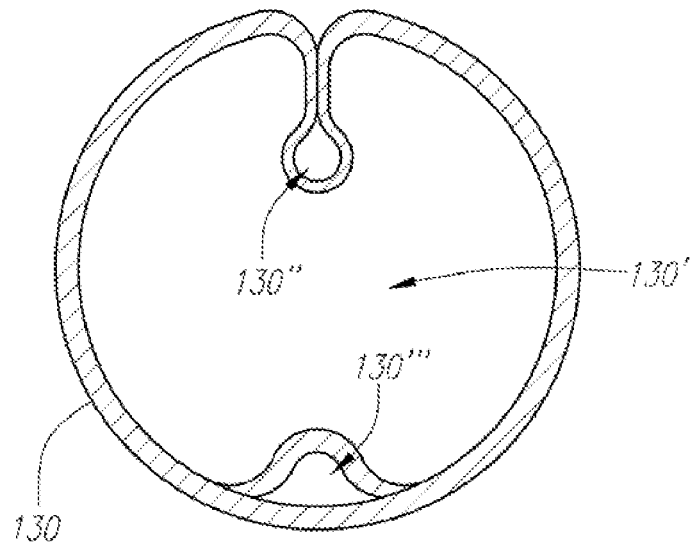

FIGS. 30A and 30B illustrate yet another configuration of the distal end of the apparatus 109. In this embodiment, the flexible sheath 130 forms first, second and third lumens 130,' 130," 130.'" The first or primary lumen 130' may be used to receive an instrument, such as an electrical pacing lead, and the like. The second lumen 130" may receive the elongate stiffening member 120 (not shown). The third lumen 130'" may be used, for example, to receive an instrument, such as a guidewire and the like. Alternatively, the third lumen 130'" may be used to receive or contain a contrast solution (not shown) for imaging the location of the apparatus 109 within a patient. The third lumen 130'" may enclose the second lumen 130," as is shown in FIG. 30A, or may be opposite the second lumen 130," shown in FIG. 30B.

Figure 31A:
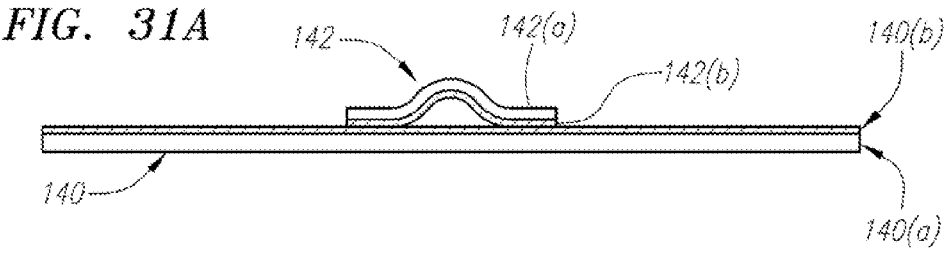
FIGS. 31A-31C are cross-sectional views showing a method for constructing a flexible sheath.
Figure 31B:
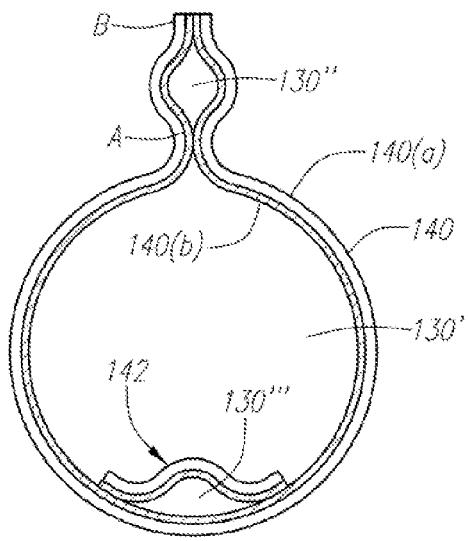
Figure 31C:
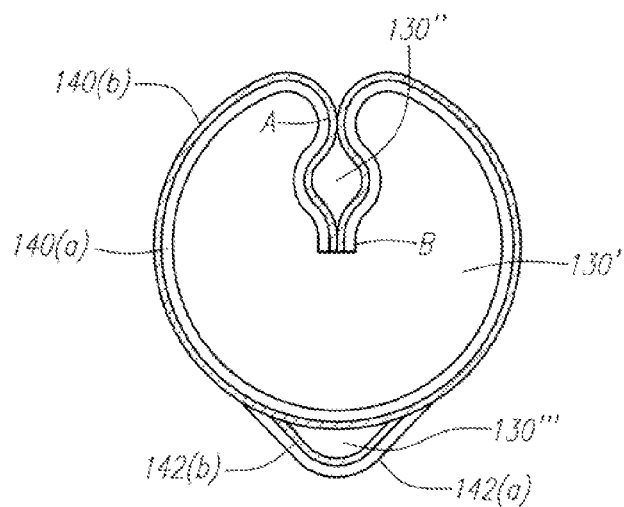

FIGS. 31A, 31B, and 31C illustrate a method for constructing a flexible sheath 130 having first, second, and third lumens 130,' 130," and 130'" out of a cast film. With reference to FIG. 31A, a film 140 may be provided having a base layer 140(a) of PTFE and a surface layer of FEP 140(b). If a third lumen 130'" is desired, a separate layer of film 142 having a base layer 142(a) of PTFE and a surface layer of FEP 142(b) may be provided adjacent to film 140. The smaller layer of film 142 is oriented to place the two FEP surface layers 140(b), 142(b) in contact with one another. A space 143 or lumen may also be formed between the two layers of film 140, 142. The two layers of film 140, 142 may then be bonded to one another at the interfaces by, for example, heat bonding the two opposing FEP-FEP surfaces 140(b), 142(b).

After bonding the two opposing FEP-FEP surfaces 140(b), 142(b), the structure shown in FIG. 31B may be formed by folding the sheet 140 onto itself and heat bonding opposing FEP-FEP surfaces 140(b) at locations A and B as shown in FIG. 31B. In this regard, a sheath 130 may be formed having first, second, and third lumens 130,' 130," and 130.'" The first lumen 130' is preferably used to receive an instrument, such as an electrical pacing lead (not shown). The second lumen 130" is preferably used to house the elongate stiffening member 120. The third lumen 130'" is preferably used to receive or contain contrast solution for imaging the location of the apparatus 109.

FIG. 31C illustrates a sheath 130 created by inverting the structure shown in FIG. 31B. The sheath 130 may be created by pulling an end of the sheath 130 shown in FIG. 31B through the first or primary lumen 130.' This structure is particularly preferred because it places the lubricious PTFE layer 140(a) on the interior of the primary lumen 130.'

Figure 32:
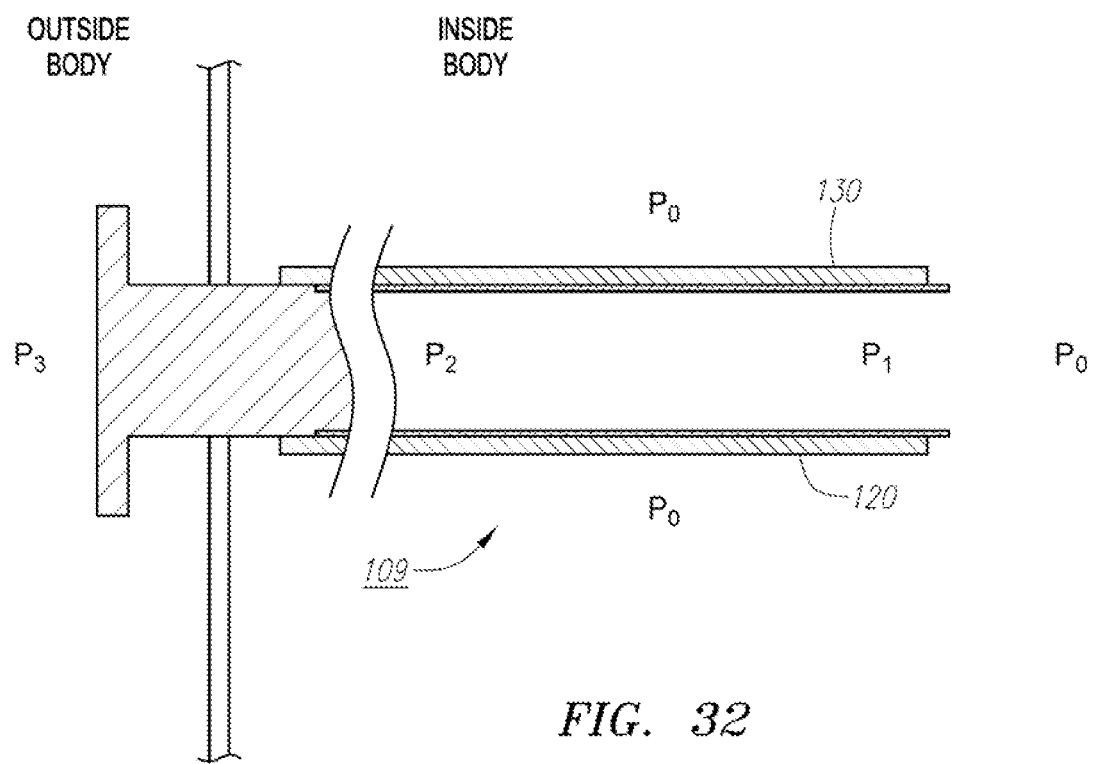
FIG. 32 is a cross-sectional side view of yet another embodiment of a flexible sheath providing an automatically sealing lumen.

FIG. 32 illustrates an auto-sealing nature of a flexible sheath 130, according to another embodiment. When placed inside a pressurized environment within the body (e.g., within a blood vessel), the flexible sheath 130 may collapse when the pressure differential between the outside of the sheath 130 and the inside of the sheath 130 is sufficient to overcome the "hoop" strength of the sheath 130.

FIG. 32 illustrates several different pressures experienced by the apparatus 109 100 located within a blood vessel. $P_0$ represents the blood pressure of the blood vessel. $P_1$ represents the pressure at the distal end of the sheath 130 while $P_2$ represents the pressure at a proximal region of the sheath 130. $P_3$ represents atmospheric pressure. Given that $P_1 > P_2 > P_3$ and at the distal tip of the sheath 130 $P_0 \approx P_1$, then the sheath 130 may collapse when the differential between P2 and $P_0$ is sufficient to overcome the resilient or "hoop" strength of the sheath 130.

In thin-walled materials with a low "hoop" strength, the collapse of the sheath 130 occurs readily. The collapse of the sheath 130 (either on itself or around another structure such as an elongate stiffening member 120) may prevent blood loss and/or further reinforce the pressure differential that keeps the sheath material in the collapsed configuration.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

We claim:

1. An apparatus for providing access to a body lumen, comprising:
    a tubular proximal portion formed by a self-supporting wall that does not significantly expand or collapse during use, the proximal portion having a length defined from a proximal end to a distal end thereof and a first lumen extending from the proximal end to the distal end; and an expandable distal portion being fixedly attached directly to the wall of the tubular proximal portion, at the distal end of the tubular proximal portion, and extending distally from the distal end of the tubular proximal portion over a length that is less than the length of the proximal portion, the expandable distal portion including an expandable sheath and a stiffening member;

wherein the expandable sheath includes a distal terminal end and defines a second lumen that extends distally from the distal end of the proximal tubular portion to a distal terminal opening of the second lumen, the second lumen being in fluid communication with the first lumen of the tubular proximal portion;

the stiffening member is attached directly to the expandable sheath so as to extend alongside the second lumen, the stiffening member extending distally from the distal end of the tubular proximal portion and beyond the distal terminal opening of the second lumen; and the distal terminal opening of the second lumen is defined by a portion of a perimeter of the distal terminal end of the expandable sheath that becomes spaced apart from the stiffening member when the sheath is expanded, the distal terminal opening of the sheath lumen allowing passage therethrough, alongside the stiffening member, of a medical instrument into the body lumen, the medical instrument having been passed through the first lumen and the second lumen.

2. The apparatus of claim 1, wherein the expandable sheath comprises a sheet of material whose edges are attached to the stiffening member.

3. The apparatus of claim 1, wherein the expandable sheath includes another lumen, and the stiffening member is disposed at least partially within the other lumen.

4. The apparatus of claim 1, wherein the length of the proximal tubular portion is about one hundred ten centimeters or more.

5. The apparatus of claim 1, wherein the length of the proximal tubular portion is sufficient to reach a right atrium from a subclavian percutaneous entry site.

6. The apparatus of claim 1, wherein the length over which the expandable distal portion extends distally from the distal end of the tubular proximal portion is between about ten and fifty centimeters.

7. The apparatus of claim 1, wherein the length over which the expandable distal portion extends distally from the distal end of the tubular proximal portion is not more than about thirty centimeters.

8. The apparatus of claim 1, wherein the stiffening member includes a lumen extending at least between the distal end of the tubular member and beyond the distal terminal opening of the second lumen.

9. The apparatus of claim 1, wherein the stiffening member of the expandable distal portion is integral with the wall of the tubular proximal portion.

* * * * *